United States Patent
Cosse et al.

(10) Patent No.: US 9,949,806 B2
(45) Date of Patent: Apr. 24, 2018

(54) ORTHODONTIC BRACKET ASSEMBLIES WITH TORQUE-ADJUSTING DRUMS

(71) Applicant: Christopher C. Cosse, Shreveport, LA (US)

(72) Inventors: Christopher C. Cosse, Shreveport, LA (US); Calvin N. Corpus, Corona, CA (US)

(73) Assignee: Christopher C. Cosse, Shreveport, LA (US)

( * ) Notice: Subject to any disclaimer, the term of this patent is extended or adjusted under 35 U.S.C. 154(b) by 423 days.

(21) Appl. No.: 14/215,237

(22) Filed: Mar. 17, 2014

(65) Prior Publication Data

US 2014/0272751 A1    Sep. 18, 2014

Related U.S. Application Data

(60) Provisional application No. 61/798,272, filed on Mar. 15, 2013.

(51) Int. Cl.
*A61C 7/28* (2006.01)
*A61C 7/02* (2006.01)
*A61C 7/14* (2006.01)

(52) U.S. Cl.
CPC .............. *A61C 7/285* (2013.01); *A61C 7/02* (2013.01); *A61C 7/141* (2013.01)

(58) Field of Classification Search
CPC .... A61C 7/12–7/18; A61C 7/22; A61C 7/285; A61C 7/287; A61C 7/30; A61C 7/141
See application file for complete search history.

(56) References Cited

U.S. PATENT DOCUMENTS 1,280,628 A   10/1918 Angle
1,821,171 A    9/1931 Atkinson
(Continued)

FOREIGN PATENT DOCUMENTS

WO    WO 95/09580 A1    4/1995
WO    WO 2011/141973 A1    11/2011

OTHER PUBLICATIONS

English language abstract of PCT Patent Application Publication No. WO 95/09580 A1, European Patent Office, Apr. 13, 1995.

*Primary Examiner* — Edward Moran
(74) *Attorney, Agent, or Firm* — DASCENZO Intellectual Property Law, P.C.

(57) ABSTRACT

Orthodontic bracket assemblies with torque-adjusting drums. The drum defines at least a majority of the archwire slot of the corresponding bracket assembly, and the drum may be selectively rotated about its longitudinal axis to adjust the prescriptive force that is applied to a patient's tooth during orthodontic use of the bracket assembly. The bracket assembly includes a positioning assembly that selectively retains the drum in a selected orientation relative to the base of the bracket assembly, thereby defining a prescription to be imparted by the bracket assembly to a patient's tooth. In some embodiments, the bracket assembly includes a biasing mechanism that selectively urges the positioning assembly to a position in which the drum is, or is not, retained in a selected position. In some embodiments, the bracket includes a release mechanism that selectively disengages the positioning assembly to permit adjustment of the drum.

18 Claims, 8 Drawing Sheets

(56) References Cited

U.S. PATENT DOCUMENTS

| | | |
|---|---|---|
| 3,435,527 A | 4/1969 | Kesling |
| 3,721,005 A | 3/1973 | Cohen |
| 3,772,787 A | 11/1973 | Hanson |
| 4,077,126 A | 3/1978 | Pletcher |
| 4,139,945 A | 2/1979 | DiGiulio |
| 4,144,642 A | 3/1979 | Wallshein |
| 4,171,568 A | 10/1979 | Förster |
| 4,197,642 A | 4/1980 | Wallshein |
| 4,243,387 A | 1/1981 | Prins |
| 4,249,897 A | 2/1981 | Anderson |
| 4,353,692 A | 10/1982 | Karrakussoglu |
| 4,371,337 A | 2/1983 | Pletcher |
| 4,419,078 A | 12/1983 | Pletcher |
| 4,492,573 A | 1/1985 | Hanson |
| 4,496,317 A | 1/1985 | Hulsey |
| 4,531,911 A | 7/1985 | Creekmore |
| 4,559,012 A | 12/1985 | Pletcher |
| 4,561,844 A | 12/1985 | Bates |
| 4,597,739 A | 7/1986 | Rosenberg |
| 4,614,497 A | 9/1986 | Kurz |
| 4,655,708 A | 4/1987 | Fujita |
| 4,698,017 A | 10/1987 | Hanson |
| 4,712,999 A | 12/1987 | Rosenberg |
| 4,850,865 A | 7/1989 | Napolitano |
| 4,867,678 A | 9/1989 | Parker |
| 4,878,840 A | 11/1989 | Reynolds |
| 5,094,614 A | 3/1992 | Wildman |
| 5,302,121 A | 4/1994 | Gagin |
| 5,322,435 A | 6/1994 | Pletcher |
| 5,358,402 A | 10/1994 | Reed et al. |
| 5,380,196 A | 1/1995 | Kelly et al. |
| 5,562,444 A | 10/1996 | Heiser et al. |
| 5,618,175 A | 4/1997 | Reher et al. |
| 5,711,666 A | 1/1998 | Hanson |
| 5,857,850 A | 1/1999 | Voudouris |
| 5,954,502 A | 9/1999 | Tuenge et al. |
| 6,193,508 B1 | 2/2001 | Georgakis |
| 6,264,469 B1 | 7/2001 | Moschik |
| 6,302,688 B1 | 10/2001 | Jordan et al. |
| 6,305,932 B1 | 10/2001 | Mottate |
| 6,358,045 B1 | 3/2002 | Farzin-Nia et al. |
| 6,582,226 B2 | 6/2003 | Jordan et al. |
| 6,632,088 B2 | 10/2003 | Voudouris |
| 6,655,957 B2 | 12/2003 | Abels et al. |
| 6,659,766 B2* | 12/2003 | Abels .................... A61C 7/125 433/10 |
| 7,192,274 B2 | 3/2007 | Stadtmiller et al. |
| 7,306,458 B1 | 12/2007 | Lu |
| 7,431,586 B1 | 10/2008 | Silverman |
| 7,771,640 B2 | 8/2010 | Cosse |
| 7,819,660 B2 | 10/2010 | Cosse |
| 7,963,768 B2 | 6/2011 | Hilliard |
| 8,272,867 B2 | 9/2012 | Chikami et al. |
| 8,333,586 B2 | 12/2012 | Kantomaa |
| 8,337,198 B2 | 12/2012 | Cosse |
| 8,366,440 B2 | 2/2013 | Bathen et al. |
| 8,550,814 B1 | 10/2013 | Collins |
| 2002/0110771 A1 | 8/2002 | Abels et al. |
| 2005/0239012 A1 | 10/2005 | Bathen et al. |
| 2006/0051721 A1 | 3/2006 | Carriere |
| 2008/0293005 A1 | 11/2008 | Rahlis et al. |
| 2009/0004619 A1 | 1/2009 | Oda et al. |
| 2011/0183280 A1 | 7/2011 | Cosse et al. |
| 2011/0311934 A1 | 12/2011 | Kantomaa |
| 2012/0064475 A1 | 3/2012 | Lewis et al. |
| 2012/0122050 A1 | 5/2012 | Bathen et al. |
| 2012/0308952 A1 | 12/2012 | Cosse |
| 2012/0315593 A1 | 12/2012 | Ramos-de-la-Peña et al. |
| 2013/0078595 A1 | 3/2013 | Solano Reina et al. |
| 2014/0205962 A1* | 7/2014 | Damon .................... A61C 7/22 433/13 |

* cited by examiner

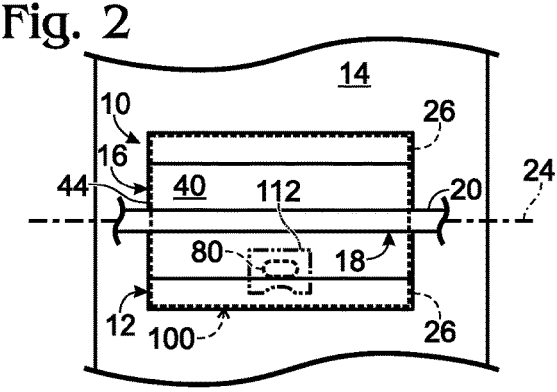
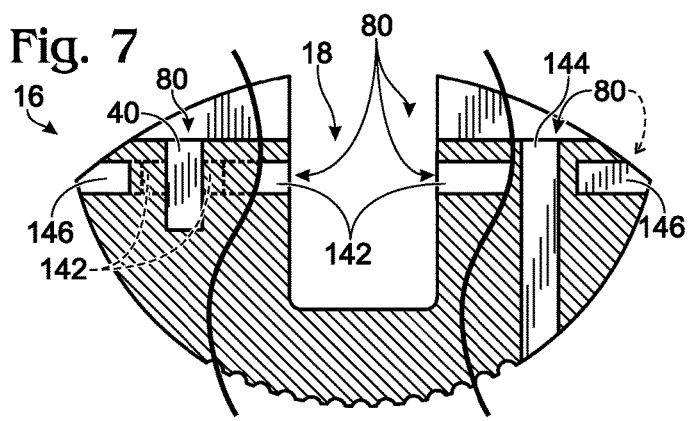
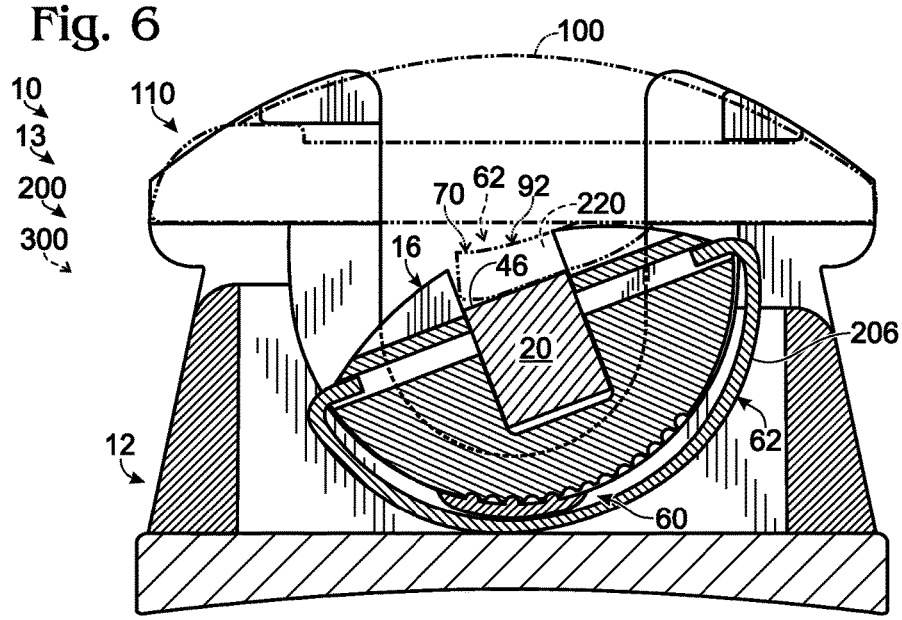

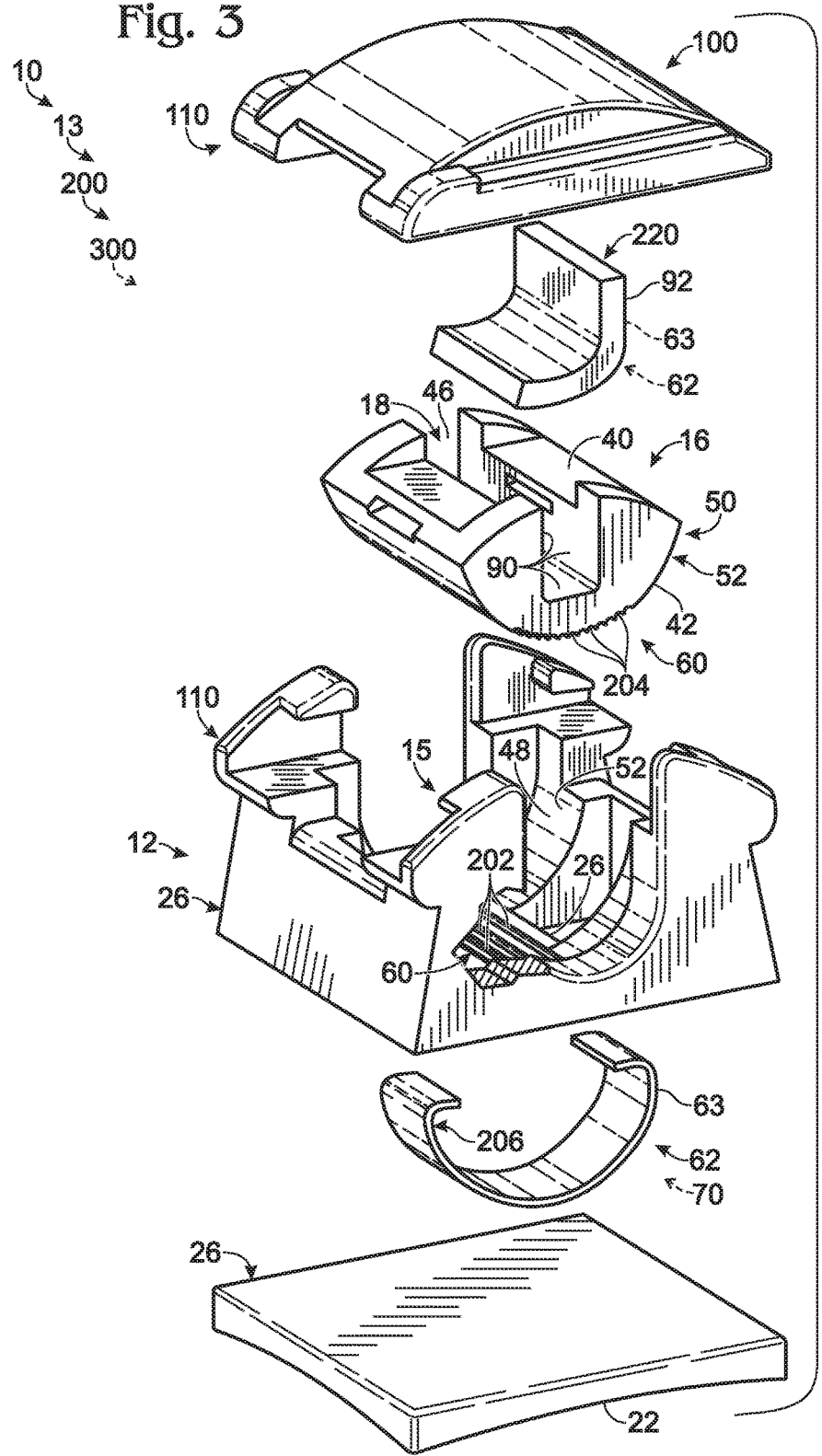

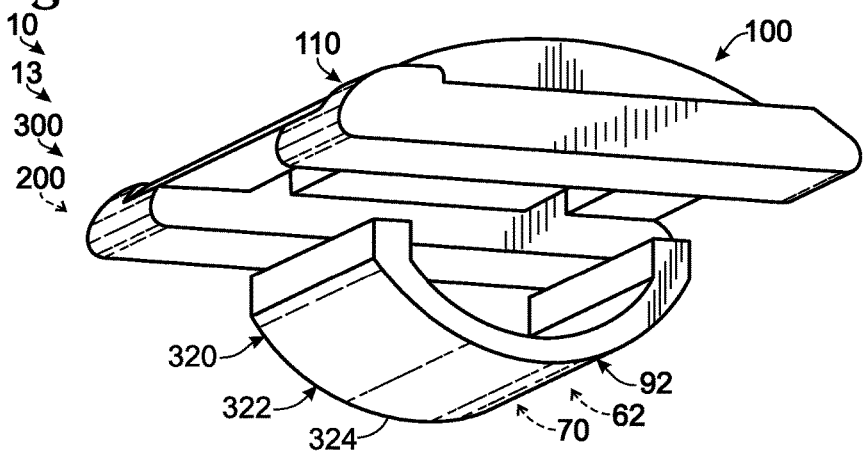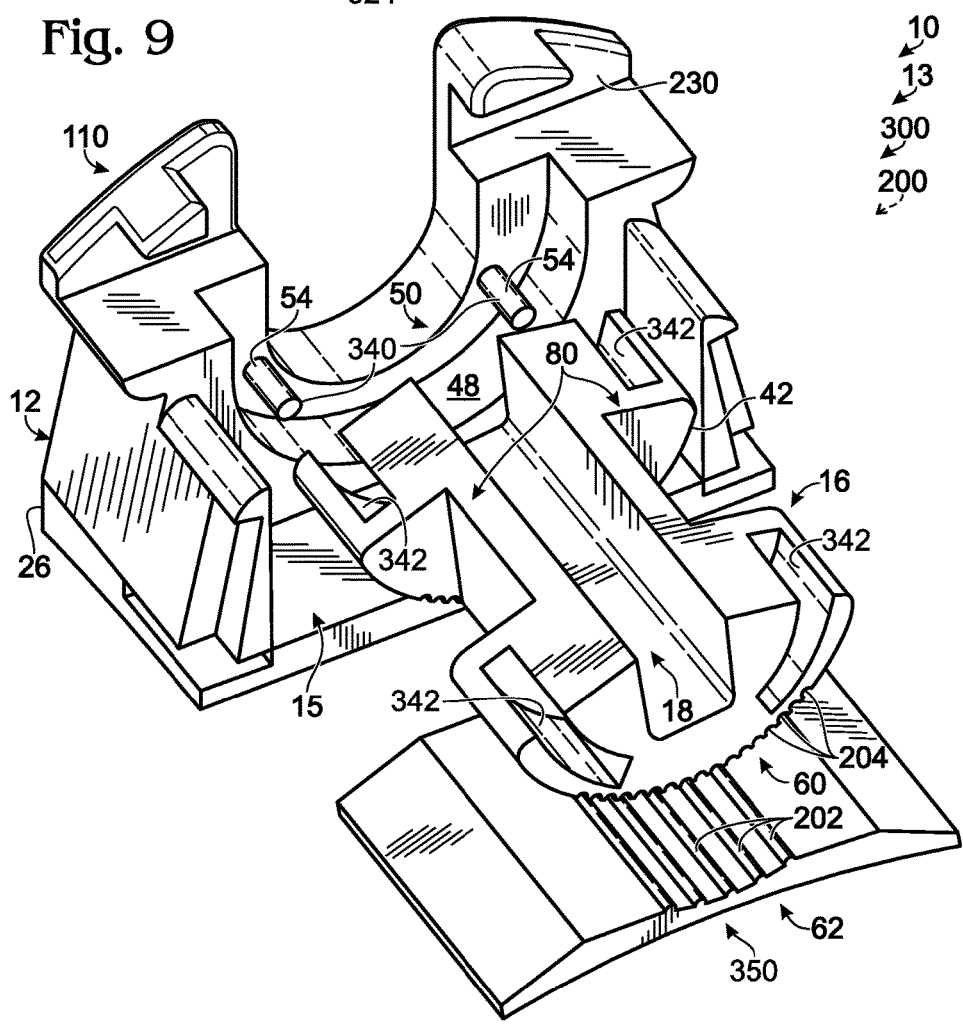

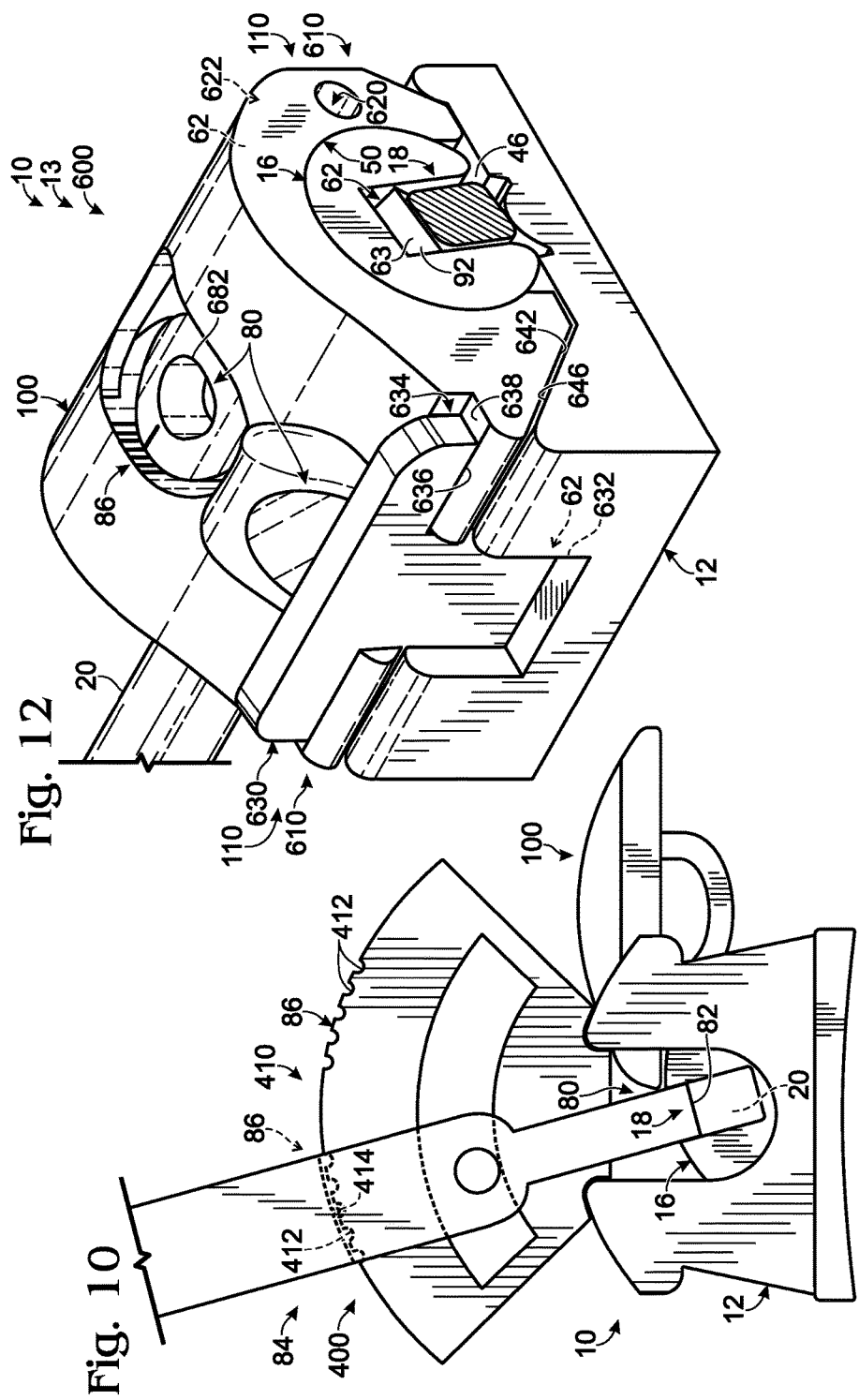

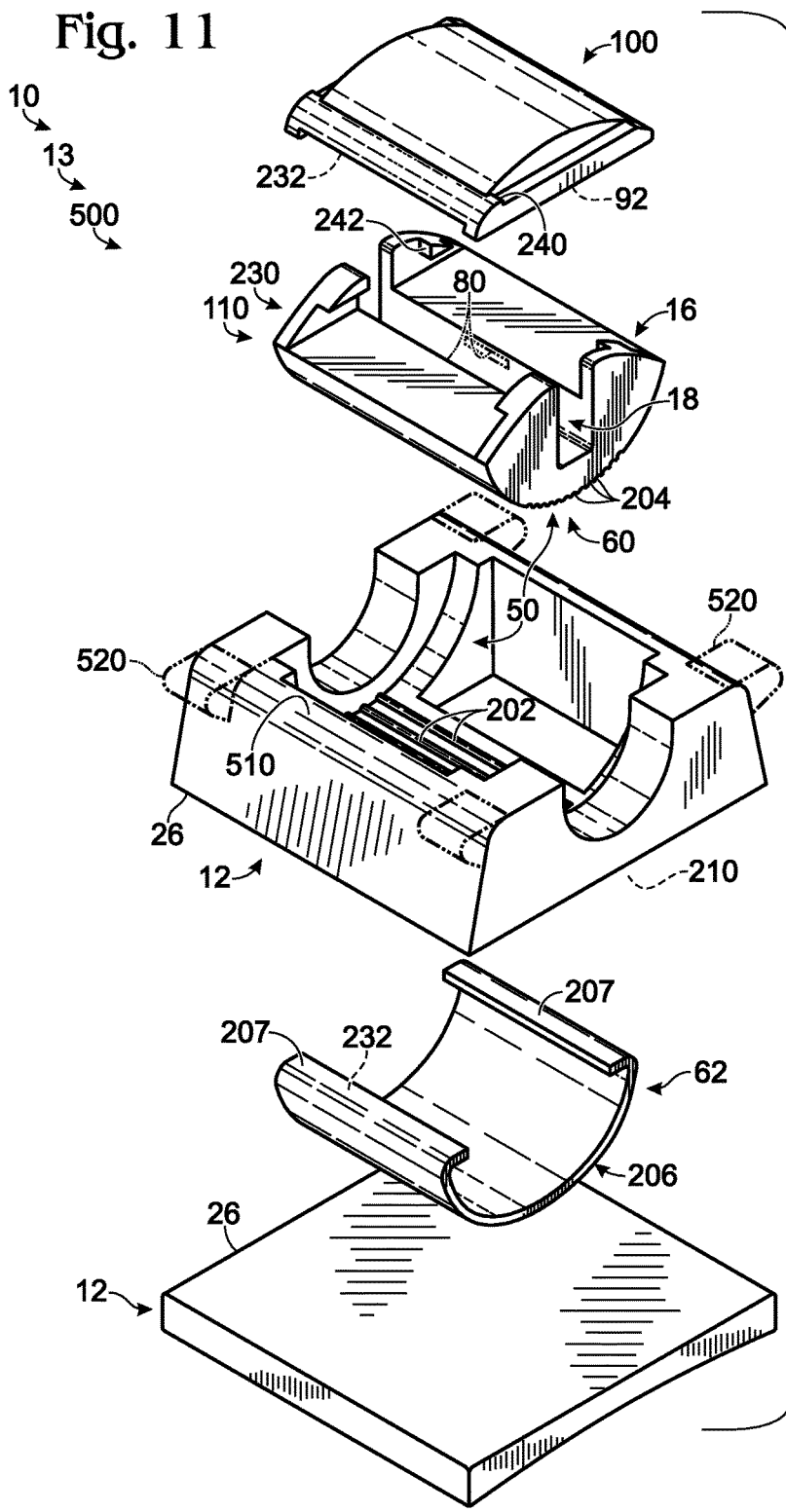

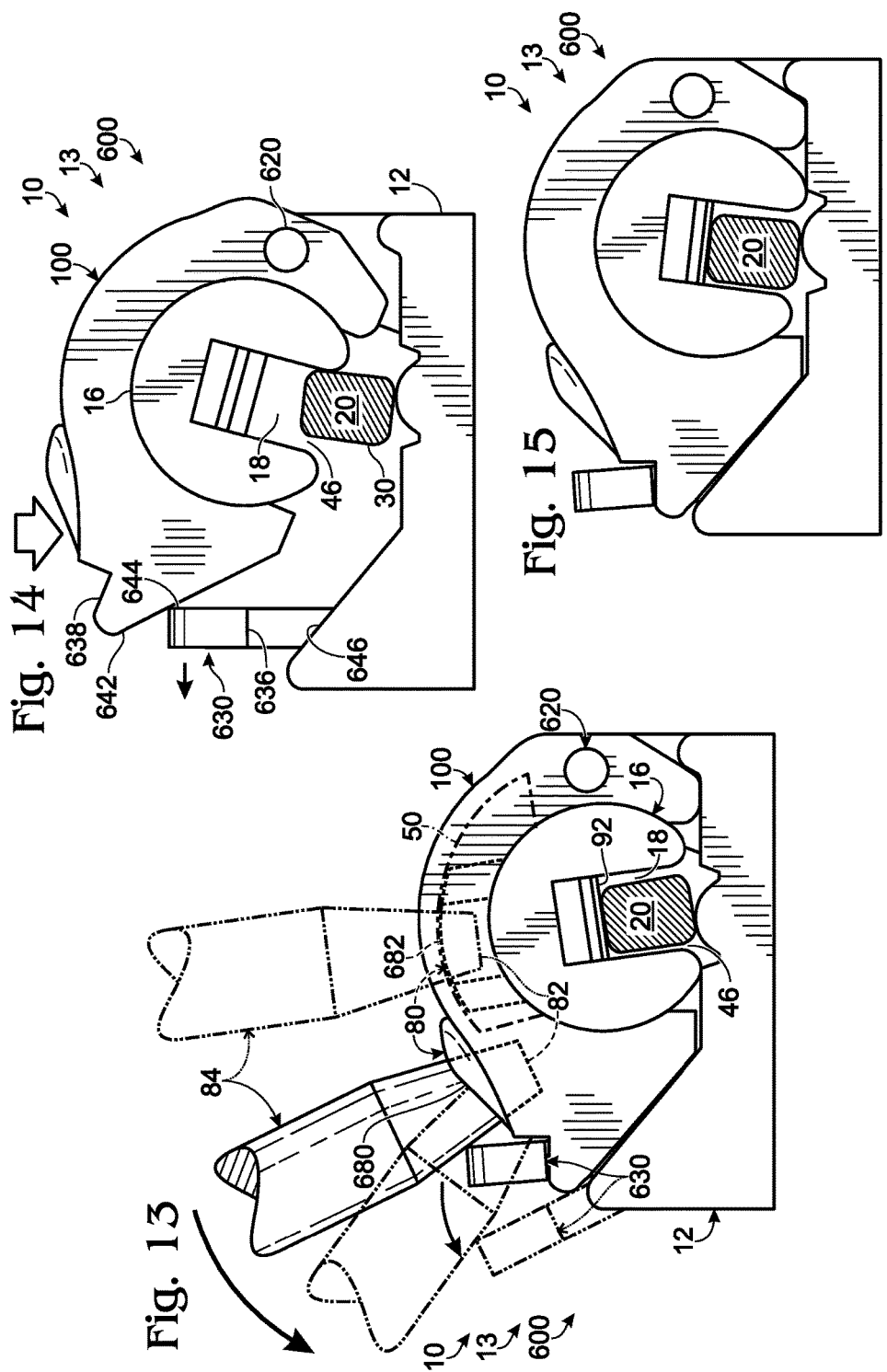

ORTHODONTIC BRACKET ASSEMBLIES WITH TORQUE-ADJUSTING DRUMS

RELATED APPLICATION

This application claims priority under 35 U.S.C. § 119 to similarly entitled U.S. Provisional Patent Application Ser. No. 61/798,272, which was filed on Mar. 15, 2013 and the complete disclosure of which is hereby incorporated by reference.

FIELD OF THE DISCLOSURE

The present disclosure is directed generally to the orthodontic field, and more particularly to orthodontic brackets with torque-adjusting drums.

BACKGROUND OF THE DISCLOSURE

Orthodontic brackets are typically small, slotted devices for use during orthodontic treatment. The brackets usually are configured for attachment to the front surfaces of teeth, either by directly cementing the bracket to a tooth surface or by bonding the bracket to a metal band that encircles the tooth, though they also may be attached to the back surfaces of teeth. The slots in the brackets, which may be referred to as archwire slots or archwire passages, are disposed horizontally or generally horizontally and are configured to receive an archwire. Traditionally, an archwire is a resilient, curved piece of wire that may be bent or twisted prior to installation in the bracket slots, with an archwire typically extending through the slots of all of the orthodontic brackets that are attached to a patient's upper or lower teeth. The engagement between the archwire and the brackets creates corrective, or prescriptive, forces that are directed to the teeth by the orthodontic brackets to urge the teeth into a correct or desired alignment or occlusion.

The archwire may be secured in a bracket's archwire slot by a variety of mechanisms, such as depending on the bracket's configuration. For example, a "ligating" bracket typically requires a separate fastener, such as a ligature wire or elastic band, which is tied or otherwise positioned around ligating structures, such as tie wings, on the bracket body to secure the archwire in place. A "self-ligating" bracket, on the other hand, typically includes a clamp, gate, or other self-locking closure mechanism, such as a closeable bracket slot, that allows such a bracket to retain the archwire without requiring the use of ligatures or other separate fasteners.

Expressed in slightly different terms, conventional ligating and self-ligating orthodontic brackets define an archwire slot with an opening into which the archwire may be inserted into the slot (other than by axially inserting the archwire through the opposed ends of the archwire slot). The opening of the archwire slot typically extends in a plane generally parallel to the base of the bracket and/or surface of the corresponding tooth to which the bracket is secured. The archwire typically is inserted into the archwire slot by inserting the wire through the opening. However, a conventional ligating bracket requires a ligature or other structure that is not part of the bracket to obstruct or otherwise close the opening to prevent removal of the archwire therethrough. In contrast, a conventional self-ligating bracket includes a movable gate or closure that is coupled to the body of the bracket for relative movement with respect to the body without removal or separation of the gate or closure from contact with the body. The gate or closure is configured to be slid, pivoted, or otherwise moved from an open position, in which an archwire may be inserted into the archwire passage through the opening, to a closed position, in which the opening of the archwire passage is closed or otherwise obstructed to prevent removal of the archwire therethrough.

Regardless of whether the bracket is a self-ligating bracket or whether the bracket requires separate fasteners or ligatures to secure an archwire in the bracket's archwire slot, orthodontic treatment of a patient's teeth typically requires periodic adjustment of the forces that are imparted to the patient's teeth by the installed orthodontic brackets, archwire(s), etc. These adjustments may include changing the magnitude and/or direction of the forces that are imparted to the patient's teeth, such as to adjust the degree to which torque, tip, and/or rotational forces are imparted to the patient's teeth to change the angulation, inclination, rotation, height and/or location of the teeth in order to move the teeth toward an optimal occlusion. As used herein, tipping forces refer to forces applied to the tooth in the mesio-distal direction. Thus, tipping forces may impact angulation. Torsional forces refer to forces applied to the tooth by an archwire that is in torsion within the archwire passage. Thus, torsional forces tend to rotate the tooth in the bucco-lingual direction and may impact inclination. Rotational forces refer to applied forces that tend to rotate the tooth about its long axis.

Adjustment of some of these forces, including torsional (i.e., torque) forces, typically requires removal of the archwire from the corresponding brackets, along with replacement of the archwire and, in some cases, removal and replacement of the bracket. Even with a bracket that permits the applied forces to be adjusted without removal of the bracket from a patient's tooth, fine adjustment of these forces still may be challenging.

SUMMARY OF THE DISCLOSURE

Orthodontic bracket assemblies with torque-adjusting drums. The orthodontic bracket assemblies include a base, which is configured to be secured to a tooth, and a torque-adjusting drum that is operatively coupled to the base for selective rotation relative to the base. The torque-adjusting drum includes, or at least defines a portion of, an archwire slot, or archwire passage, that is sized and operatively oriented to receive an archwire during use of the orthodontic bracket assembly to apply a prescriptive force to a patient's teeth. The torque-adjusting drum is configured to be selectively rotated relative to the base within a range of operative positions, with the relative position of the drum with respect to the base altering the orientation of the archwire slot relative to the base, and thereby relative to the tooth to which the base is secured. Accordingly, adjusting the relative rotation of the drum relative to the base adjusts the torque that is applied to the patient's tooth during prescriptive use of the bracket assembly. The drum may be selectively rotated relative to the base about a rotational axis, such as which extends generally parallel to the longitudinal axis of the archwire slot.

In some embodiments, the orthodontic bracket assembly is configured to permit adjustment of the applied (and/or prescribed or selected) torque without requiring removal of an archwire that is located within the archwire slot. In some embodiments, the orthodontic bracket assembly includes a socket or other receiver that is configured to be operatively engaged by an adjustment tool that facilitates incremental adjustment of the torque responsive to corresponding incremental movements of the tool. In some embodiments, the drum is selectively retained in a selected orientation within the range of positions by a drum retainer that is associated with the base of the bracket assembly. In some such embodiments, the bracket assembly includes a clutch, or release, mechanism that is configured to selectively disengage the drum from the drum retainer to permit relative rotation or adjustment therebetween. In some embodiments, the clutch mechanism is biased, such as spring-biased, to urge the drum to a disengaged position or an engaged position. In some such embodiments, the bracket assembly includes a socket, or receiver, that is configured to receive an operative portion of an adjustment tool that is inserted into the receiver to selectively actuate the release mechanism and to facilitate measured adjustment of the rotational orientation of the drum relative to the base.

In some embodiments, the orthodontic bracket assembly includes an archwire biasing mechanism that is configured to bias or otherwise urge the archwire within the archwire slot. In some such embodiments, the archwire biasing mechanism is, or includes, at least one of a spring member, an elastomeric member, and a compliant member.

In some embodiments, the bracket assembly is a ligating bracket assembly, whereas in other embodiments, the bracket assembly is a self-ligating bracket assembly that includes a gate, or closure, that selectively obstructs and/or permits access to the archwire slot by an archwire. In some embodiments, the drum is coupled to the base and thereby does not move relative to the gate when the gate moves between open and closed configurations relative to the base. In some self-ligating embodiments, the drum is coupled for movement with the gate as the gate moves relative to the base. In some self-ligating embodiments, the gate is coupled to the drum and thus moves with the drum as the drum is selectively rotated relative to the base. In some self-ligating embodiments, the bracket assembly includes a clasp that is configured to automatically engage and retain the gate in a closed configuration.

BRIEF DESCRIPTION OF THE DRAWINGS

FIG. 2 is a schematic top plan view of the orthodontic bracket assembly of FIG. 1.

FIG. 3 is an exploded, partial fragmentary view of a less schematic example of an orthodontic bracket assembly according to the present disclosure.

FIG. 6 is a cross-sectional view of the bracket assembly of FIG. 4 with the torque-adjusting drum repositioned to a different retained position.

FIG. 7 is a cross-sectional view of a torque-adjusting drum that may be utilized with orthodontic bracket assemblies according to the present disclosure.

FIG. 8 is an exploded view of a closure that may be utilized in a self-ligating orthodontic bracket assembly according to the present disclosure.

FIG. 9 is an exploded view of a base, torque-adjusting drum, and positioning assembly that may be utilized in an orthodontic bracket assembly according to the present disclosure.

FIG. 10 is a simplified side elevation view of an orthodontic bracket assembly according to the present disclosure and a fragmentary tool that may be utilized to assist in adjusting the torque-adjusting drum to a desired, or selected, retained position.

FIG. 11 is an exploded view of a closure and torque-adjusting drum that may be utilized in an orthodontic bracket assembly according to the present disclosure.

FIG. 12 is a perspective view of another orthodontic bracket assembly according to the present disclosure in a retained position.

FIG. 13 is a side elevation view of the bracket assembly of FIG. 12.

FIG. 14 is a perspective view of the orthodontic bracket assembly of FIG. 12 in an adjustment position.

FIG. 15 is a side elevation view of the orthodontic bracket assembly of FIG. 12 in a different retained position.

DETAILED DESCRIPTION AND BEST MODE OF THE DISCLOSURE

Figure 1:
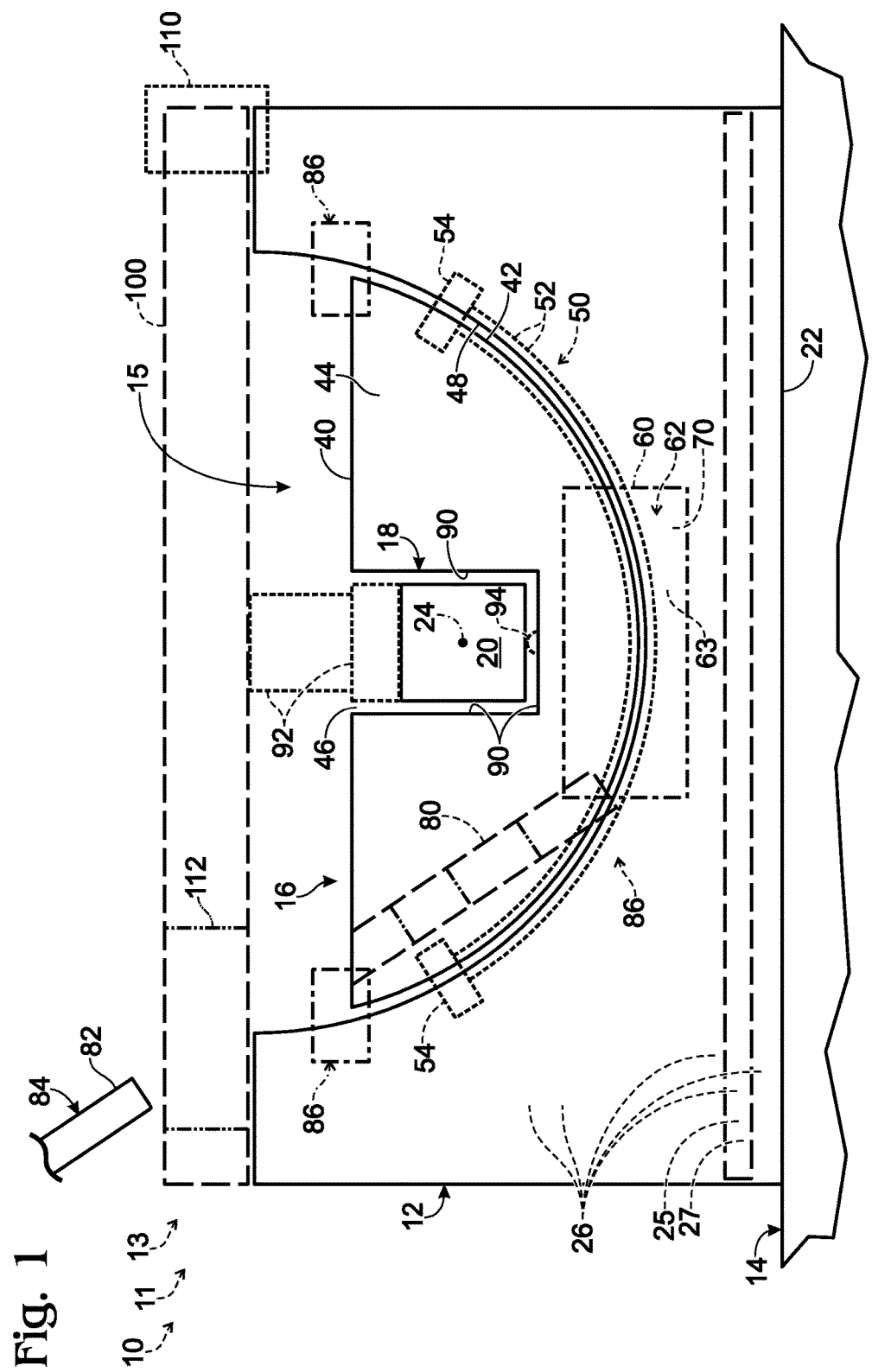
FIG. 1 is a schematic side elevation view of an orthodontic bracket assembly according to the present disclosure.

FIGS. 1 and 2 provide schematic views of orthodontic bracket assemblies according to the present disclosure, with such bracket assemblies indicated generally at 10. Bracket assembly 10 includes a base 12 that is configured to be secured to a patient's tooth 14 and which defines an enclosure 15 that is sized to receive a torque-adjusting drum 16. Bracket assembly 10 further includes such a torque-adjusting drum 16, which is received into enclosure 15 and coupled for selective rotational movement relative to the base. Enclosure 15 additionally or alternatively may be referred to as drum-receiving recess 15, a drum-receiving compartment 15, a drum receptacle 15, an internal compartment 15, an internal region 15, and/or a central chamber 15 of the bracket assembly 10 and/or of base 12.

Torque-adjusting drum 16 is configured to be selectively rotated relative to the base and defines at least a portion of an archwire passage, or archwire slot, 18 through which an archwire extends during orthodontic use of the bracket assembly. As discussed in more detail herein, adjustment of the rotational alignment of the drum relative to the base adjusts the rotational alignment of the archwire slot, and thus of any archwire 20 that is operatively received within the archwire slot, relative to the base. It follows that this adjustment also is relative to any tooth 14 to which the base is operatively secured, thereby altering the prescription imparted to the tooth during orthodontic use of the bracket assembly. Torque-adjusting drum 16 additionally or alternatively may be referred to herein as a torsion-adjusting drum, an archwire-receiving drum, an archwire-receiving member, a torque-adjusting member, an axially rotatable member that includes the bracket's archwire slot, a rotatable member that includes at least a portion of (and optionally all of) the bracket assembly's archwire slot, a rotatable archwire assembly, an axially rotatable archwire assembly, and/or a rotatable archwire passage.

The prescription of the bracket assembly refers to the forces that are imparted to a patient's tooth during orthodontic use of the bracket assembly. The prescription additionally or alternatively may be referred to as the applied forces, the prescriptive forces, the corrective forces, and/or simply as the forces that are imparted to the patient's tooth during orthodontic use of the bracket assembly. This rotational adjustment provides a corresponding adjustment (and/or means for adjusting) of the torque, or torsional force, that is applied to the tooth during prescriptive use of the bracket assembly. As used herein, "prescriptive use" and/or "orthodontic use" refer to use of a bracket assembly that is secured to a patient's tooth and which contains an archwire operatively secured within the bracket assembly's archwire slot to apply forces to the patient's tooth to alter the relative orientation of the patient's tooth in the patient's mouth. Similarly, "operatively," when used to describe a relationship between two or more components or elements, refers to the functionality for which the components or elements are designed to be used, assembled, mounted, coupled, etc.

In general, elements that are likely to be included in a given (i.e., particular) embodiment are illustrated in solid lines in FIGS. 1 and 2, while elements that are optional to a given embodiment are illustrated in dashed lines. However, elements that are shown in solid lines are not essential to all embodiments, and an element shown in solid lines may be omitted from a particular embodiment without departing from the scope of the present disclosure. Elements that serve a similar, or at least substantially similar, purpose are labeled with like numbers in the Figures of the present disclosure, and these elements may not be discussed in detail herein with reference to each of the Figures. Similarly, all elements may not be labeled in each of the Figures, but reference numerals associated therewith may be utilized herein for consistency. Elements, components, and/or features that are discussed herein with reference to one or more of the Figures may be included in and/or utilized with any of the Figures without departing from the scope of the present disclosure.

Base 12 is configured to be secured to a patient's tooth, either directly, such as by bonding or otherwise adhesively securing the base to the tooth, or indirectly, such as by securing or otherwise mounting the base on a band that is secured to, or around, the patient's tooth. Accordingly, base 12 may be described as including a tooth-engaging and/or tooth-facing surface, or mounting surface, 22. Base 12 provides a stable foundation for the components of bracket assembly 10 relative to the patient's tooth to which the base is secured. Although only a portion of tooth 14 is schematically illustrated in FIGS. 1 and 2, it should be understood that base 12 typically is mounted to the tooth such that the long, or longitudinal, axis 24 of archwire slot 18 extends transverse to the long axis (extending from the root to the tip) of the tooth. Base 12 of the bracket assembly additionally or alternatively may be referred to herein as the housing 12, body 12, frame 12, and/or drum-receiving member 12 of the bracket assembly.

Base 12 may be formed as a monolithic or other unitary, or one-piece, structure, although it also is within the scope of the present disclosure that the base may be formed from and/or include two or more base (or housing) members 26. This is illustrated schematically in FIG. 1 by a series of dashed lead lines associated with reference numeral 26. In some such embodiments, these base members, or base components, 26 may be secured in a fixed orientation relative to each other, such as after manufacturing of the base members, during assembly of bracket assembly 10, or after assembly of bracket assembly 10. Thus, after the base is assembled, the base members 26 function as a single, unitary structure.

In other embodiments, the base members may be configured to be selectively repositioned relative to each other, such as to adjust a property of the bracket assembly and/or the prescriptive forces provided thereby during prescriptive use of the bracket assembly. For example, relative translation, rotation, and/or angulation of one or more of the base members relative to the rest of the base and/or relative to tooth 14 may adjust the relative position of the archwire slot (compared to its position prior to this movement of one or more of the base members) and thereby alter the prescriptive force provided by the bracket assembly during prescriptive use thereof.

This optional additional adjustment of the orientation of portions of the base relative to the tooth to which the bracket is secured is illustrated schematically in FIG. 1 by the inclusion of an optional tip adjustment mechanism 25 and/or an optional rotation adjustment mechanism 27. Tip adjustment mechanism 25, when present, enables selective adjustment of the relative orientation of the archwire slot in the plane of the tooth (i.e., rotating about a central point of the archwire slot in a plane that extends generally parallel to the surface of the tooth, or at least the portion of the surface of the tooth to which the base is mounted). Thus, utilizing the tip adjustment mechanism may impart prescriptive forces to urge movement of the tooth in the mesio-distal direction. Rotation adjustment mechanism 27, when present, enables selective adjustment and/or angulation of the orientation of the archwire slot out of the plane of the tooth, such as by elevating one end of the archwire slot a greater or lesser distance above the surface of the tooth than the other end of the archwire slot. Thus, utilizing the rotation adjustment mechanism may impart prescriptive forces to urge rotation of the tooth about the long axis of the tooth.

Base 12 also may, but is not required to, include additional components, regions, and/or features that are conventional to orthodontic bracket bases/bodies/housings, such as appropriately shaped and/or contoured tooth-contacting surfaces, tie wings, or other suitable mounts for ligating structures, such as ligatures, orthodontic chains, powerchains, springs, elastic bands, and the like. In this regard, examples of orthodontic brackets and bracket assemblies, as well as components and uses thereof, and accessories therefor, are disclosed in U.S. Pat. No. 8,337,198 and in U.S. Patent Application Publication Nos. 2012/0308952 and 2011/0183280, the complete disclosures of which are hereby incorporated by reference. These and the subsequently incorporated patent references additionally or alternatively disclose optional additional structures, features, components, and the like that may be used with bracket assembly 10 (so long as doing so does not impair the operation and functionality expressly presented herein).

Additional examples of ligating orthodontic brackets are disclosed in U.S. Pat. Nos. 6,302,688, 6,582,226, 4,597,739, 4,878,840, 3,772,787, 4,248,588, 4,492,573, 4,614,497, 4,698,017, 1,280,628, 1,821,171, and 3,435,527, the disclosures of which are hereby incorporated by reference. Examples of self-ligating orthodontic brackets are disclosed in U.S. Pat. Nos. 6,659,766, 6,655,957, 6,358,045, 6,193,508, 5,857,850, 5,711,666, 5,562,444, 5,322,435, 5,094,614, 4,559,012, 4,531,911, 4,492,573, 4,419,078, 4,371,337, 4,077,126, 4,144,642, 4,248,588, 4,698,017, 3,772,787, 1,559,012, 1,561,844, 4,655,708, 4,419,078, 4,197,642, 4,712,999, and 4,171,568, the disclosures of which are hereby incorporated by reference. Still further additional examples of orthodontic brackets are disclosed in U.S. Pat. Nos. 7,819,660, 7,771,640, and 6,632,088, the disclosures of which are hereby incorporated by reference. The structures, features, applications, and methods of the above-identified references may be utilized with and/or incorporated into orthodontic bracket assemblies 10, and orthodontic appliance systems that include a plurality of bracket assemblies 10, according to the present disclosure to the extent that doing so does not conflict with the express provisions of the present disclosure.

As discussed, bracket assembly 10 includes a torque-adjusting drum 16 that is coupled for selective rotational movement relative to the base (and thus relative to any tooth to which the base is secured). This rotation is generally about, or at least about an axis that is parallel or generally parallel to, axis 24 of an archwire that is operatively secured within archwire slot 18. As also discussed, drum 16 defines at least a portion of the bracket assembly's archwire slot 18. Drum 16 may define portions of, and optionally more than half of, and further optionally at least 75% of, or even all of, at least two sidewalls, or walls, 90 of the archwire slot, and optionally at least three sidewalls of the archwire slot. As schematically illustrated in FIG. 1, the drum has a semicircular cross-sectional configuration, with a generally planar face 40 and an arcuate base-engagement surface 42. As illustrated, archwire slot 18 extends into the body 44 of the drum from an inlet, or archwire slot inlet, 46, in face 40. Similarly, base 12 includes, or defines, a drum-engagement surface 48 that is complimentarily configured relative to base-engagement surface 42.

It is within the scope of the present disclosure that base 12, drum 16, archwire slot 18, and the other components of bracket assembly 10 may have any suitable shape and relative size. Specifically, FIGS. 1 and 2 are schematic illustrations that are not intended to be interpreted to limit the present disclosure to only the schematically illustrated shapes and/or relative sizes. While an arcuate base-engagement surface 42 and a planar face 40 may be a suitable configuration for drum 16, other configurations may be used without departing from the scope of the present disclosure. Similarly, while drum 16 is illustrated schematically in FIG. 1 to have a semicircular cross-sectional configuration, other shapes (geometric, regular, irregular, complex, etc.) may be used within the scope of the present disclosure. Thus, even when referred to as a "drum," torque-adjusting drum 16 is not required in all embodiments to have a partially or completely cylindrical or spherical shape. In many embodiments the torque-adjusting drum will include an arcuate region that at least partially defines the rotatable path of movement of the drum. However, other configurations and shapes may be used, including configurations in which the drum is mounted on and/or includes an axle that defines the rotational path of the drum.

References herein to drum 16 defining at least a portion of archwire slot 18 of the bracket assembly relate to the fact that drum 16 includes, or defines, at least one, and often at least two or at least three of the archwire-contacting walls, or barriers, 90 that define archwire slot 18. As should be understood, the prescriptive, or corrective, forces imparted to tooth 14 may be generated by the archwire exerting forces against the bracket assembly (such as against the portions of drum 16 and/or other portions of the bracket assembly that define the archwire slot), by the bracket assembly against the archwire, or both.

While archwire slot 18 is schematically illustrated as being rectangular in FIGS. 1-2, it is within the scope of the present disclosure that archwire slot 18 may have any desired cross-sectional shape, including rectangular, square, circular, semi-circular, elliptical, triangular, trapezoidal, any polygonal or non-polygonal shape, irregular, symmetrical, monolithic, braided, uniform, and/or non-uniform, may not have a constant cross-section, or profile, and may contain internal structures that cause it to depart from an idealized geometry. It also is within the scope of the present disclosure that the archwire slot may not form a continuous perimeter around the cross-section of the archwire but simply may serve, or function, to retain the archwire within a desired location. Thus, the archwire slot may comprise and/or receive at least hook, clip, biasing member, spring, elastomer, or other structure that constrains or urges the archwire within a defined region. Archwire slot 18 additionally or alternatively may be referred to as an archwire passage and/or an archwire receiver.

To provide and/or guide the rotational movement between drum 16 and base 12, bracket assembly 10 includes a coupling mechanism 50, which additionally or alternatively may be referred to herein as a drum-coupling mechanism, a positioning system, a drum-positioning system, and/or a drum-adjustment system 50. Coupling mechanism 50 may include any suitable structure and/or number, shape, and/or configuration of components, or coupling members, 52 that are configured to define and/or guide the rotational movement of drum 16 relative to base/housing 12, such as along a range of positions, which may be rotational positions. As discussed, the range of positions may include a plurality of spaced-apart positions, which may be (pre)defined positions and/or user-selected defined positions.

Coupling mechanism 50 is depicted schematically in FIG. 1, and it is within the scope of the present disclosure that the coupling mechanism may include a plurality of coupling members 52, optionally including inter-engaging and/or complimentarily configured coupling members 52, that are associated with, mounted on, and/or formed in or on one or both of the base and the drum. As an example, coupling mechanism 50 may include, and/or coupling members 52 may be, include, and/or form a portion of, any suitable guide, track, gear, race, rail, and/or similar structure for enabling this relative, optionally rotatable, movement. As examples, one of the drum and the base may include at least one track, guide, slide, channel, race, gear, or similar path-defining structure, and the other of the drum and the base may include at least one gear, carriage, arm, pin, sled, or similar structure whose path of movement is dictated by the path-defining structure.

As discussed, torque-adjusting drum 16 may be described as being rotatably coupled to, and/or coupled for selective rotation relative to, base 12. Accordingly, coupling mechanism 50 may be described as enabling this rotational movement of the drum relative to the base, such as within a range, or path, of rotational movement. In connection with defining this range of rotational adjustment and/or rotational movement, coupling mechanism 50 optionally may further include and/or define at least one stop, or barrier, 54 that defines the end points of the range of relative rotation of the drum with respect to the base, which in turn defines end points for the range of rotational orientations of the archwire slot relative to the tooth. As examples, the drum may be configured to be selectively rotated within a range of at least 15°, at least 20°, at least 30°, at least 40°, or at least 50°, and/or less than 90°, less than 70°, less than 60°, less than 50°, less than 40°, or less than 30°. These examples of ranges are measured relative to a neutral, or zero, position in which the archwire slot is not rotated relative to the plane of the tooth and/or bracket, and these ranges optionally may be described as defining both positive and negative values. For example, a rotational range of 40° additionally or alternatively may be described as a range from −20° to +20°.

Coupling mechanism 50 may be configured to permit the drum to be adjusted to any angular value within this range, such as when the coupling mechanism utilizes a frictional or similar retainer that is infinitely adjustable within the range. However, it also is within the scope of the present disclosure that the coupling mechanism may be configured to permit the drum to be adjusted within predetermined, or predefined, increments or intervals within the overall range. Examples of such increments include 1°, 2°, 2.5°, 3°, 4°, 5°, 7.5°, 3°-8°, 4°-6°, 4°-10°, at least 2.5°, at least 3°, at least 5°, less than 10°, less than 8°, less than 6°, and/or less than 4°, although others may be used without departing from the scope of the present disclosure.

Coupling mechanism 50 may include, be associated with, and/or operatively be engaged by a positioning assembly 60 that selectively retains the drum in a selected rotational position relative to the base. It follows then that the positioning assembly 60 additionally or alternatively may be described as selectively retaining the archwire passage, and thus any archwire that is secured within the passage, in a selected, or defined, orientation and/or prescription relative to the base and/or to the tooth to which the base is mounted. Positioning assembly 60, when present, may be configured to selectively retain the torque-adjusting drum in a rotational position from a predefined, or predetermined, set of positions, or from an infinite array of positions, as discussed. As used herein, the rotational position within which the positioning assembly selectively secures, or retains, the torque-adjusting drum within the range of rotational positions may be referred to as a retained position. As discussed, the retained position may be predefined, such as within a plurality of incrementally spaced positions, and/or may be user-determined, such as when the positioning assembly frictionally or otherwise retains the torque-adjusting drum when the positioning assembly is actuated or otherwise engaged by a user, such as an orthodontist or technician.

Positioning assembly 60 includes any suitable structure for selectively, and thus releasably, securing or otherwise retaining the drum in a selected rotational position relative to the base. Accordingly, the positioning assembly may be described as being selectively moved or otherwise configured between an actuated configuration and an unactuated configuration. The locked configuration additionally or alternatively may be referred to as an engaged configuration, a locked configuration, and/or a retaining configuration. The unactuated configuration additionally or alternatively may be referred to as an unlocked configuration, a disengaged configuration, and/or an adjustment configuration. In the locked configuration, relative rotation of the drum relative to the base is prevented or otherwise restricted, whereas in the unlocked configuration, the drum may be selectively rotated relative to the base, such as within the range of positions.

In other words, the positioning assembly 60, when present, may be configured to selectively retain, or secure, a specific rotational position of the drum relative to the base, which as discussed, also defines a corresponding rotational position of the archwire slot relative to the base. As also discussed, this in turn defines a corresponding relative orientation of archwire 20 relative to the patient's tooth 14 to which the bracket assembly is secured, thereby defining the torsional and/or other prescriptive, or corrective, force to be applied to the tooth during prescriptive use of the bracket assembly. When the torque-adjusting drum is secured or otherwise retained in a selected position, which may be one of a series of defined or predetermined positions, such as by the positioning assembly 60, the drum may be described as being in a retained position. In contrast, when the drum is unretained or otherwise able to be rotated to a different position, which may be a different retained position, the drum may be described as being in an adjustment position. Thus, the positioning assembly selectively secures the drum in a retained position, and upon release of the positioning assembly, permits the drum to be repositioned, while in an adjustment position, to a different retained position.

The degree of force required to reposition the drum when in the adjustment position may vary without departing from the scope of the present disclosure. Clearly, the degree of force should be reasonable to be applied to a portion of an orthodontic bracket in a patient's mouth. In many embodiments, bracket assembly may be designed, such as via coupling mechanism 50, positioning assembly 60, and/or biasing mechanism 62 to apply sufficient frictional or other forces to the drum to require the user to apply force to the drum to rotate the drum within the range of positions. In other words, while it is within the scope of the disclosure that drum 16 may be sufficiently unrestrained and/or loose to rotate freely once moved to an adjustment position, in many embodiments, the bracket assembly may be designed to require some degree of positive applied force to rotate the drum, such as to a new selected retained position. This may enable drum to remain above, aligned with, or otherwise proximate a prior selected retained position (such as to provide a reference point to the orthodontist, technician, or other user) until positively urged from this position along the range of rotational positions.

Positioning assembly 60 additionally or alternatively may be referred to as a position-selection assembly, a rotation-selection assembly, a torque-selection assembly, a position-selection mechanism, a rotation-selection mechanism, and/or a torque-selection mechanism. Positioning assembly 60 may utilize any suitable mechanism and/or structure to selectively interlock and/or inter-engage the torque-adjusting drum and the base to restrict repositioning of the torque-adjusting drum relative to the base until the positioning assembly is disengaged or otherwise returned to an unlocked/unactuated configuration. Examples of suitable structures for a positioning assembly 60 include set screws, pins, biased pins, wedges, frictional surfaces, gears, ribs, detents, slots, catches, latches, pivotal catches, and/or teeth that may be selectively positioned to prevent further relative rotation between the drum and the base until the positioning assembly has been retracted or otherwise disengaged so that relative rotational movement between the drum and base is again permitted.

Although not required to all embodiments, positioning assembly 60, when present, may include at least one portion that engages, is mounted on/to, is coupled to, is formed in, or forms a portion of the torque-adjusting drum and at least one portion that engages, is mounted on/to, is coupled to, is formed in, or forms a portion of the base of the bracket assembly. Optionally, in embodiments of bracket assembly 10 that form a self-ligating bracket assembly 13, a portion of the positioning assembly additionally or alternatively may engage, be mounted on/to, be coupled to, be formed in, or form a portion of the subsequently discussed closure of the self-ligating bracket assembly.

As a further example, one of the drum and the base may include a rib, tooth, tab, or other projecting structure, and the other of the drum and the base may include a plurality of spaced-apart recesses, channels, catches, detents, or similar structures that are sized and/or positioned to selectively receive/engage the rib or other projecting structure. The plurality of spaced apart recesses or similar projection-receiving structure may be radially or otherwise incrementally spaced apart, such as by equal distances. When the positioning assembly is in a locked configuration, the rib or other projecting structure is sufficiently received in and/or engaged with one of the recesses or other projection-receiving structures to retain the torque-adjusting drum at the corresponding rotational position relative to the base. When the positioning assembly is in an unlocked, or disengaged, configuration, the rib or other projecting structure is sufficiently removed from and/or disengaged from the corresponding recess or other projection-receiving structure to permit rotation of the torque-adjusting drum relative to the housing, and thus positioning of the drum to an adjustment position. Upon movement of the drum to a new selected position relative to the housing, such as to a different retained position, the positioning assembly may be re-actuated, such as by inserting the rib or other projecting structure sufficiently into a recess or other projection-receiving structure to again restrict further rotational movement of the drum relative to the housing. As a further example, the positioning assembly may include a plurality of spaced-apart ribs or other projecting members, and a corresponding plurality of recesses or other projection-receiving structures. The number of recesses or other projection-receiving structures may exceed the number of ribs or other projecting structures, and in some embodiments may be 1.5, 2, 3, or more times the number of ribs or other projecting structures.

Bracket assembly 10 optionally may include at least one biasing mechanism, or biasing assembly, 62 that is configured to bias, or urge, the torque-adjusting drum to a retained position or to an adjustment position. It is within the scope of the present disclosure that the biasing mechanism, when present, may be configured to bias/urge the positioning assembly (and/or components thereof) to position/retain the drum in a retained position (or to an adjustment position, depending on the construction of the bracket assembly with which it is used). As another example, the biasing mechanism may be configured to urge the subsequently discussed release mechanism to a locked configuration or to an unlocked configuration.

Expressed in slightly different terms, when present, biasing mechanism 62 may be configured to bias the torque-adjusting drum to and/or to remain within, a retained position. In such a configuration, the biasing mechanism may be described as providing a retaining force that must be removed or overcome to configure the torque-adjusting drum from the retained position to an adjustment position. As another example, the biasing mechanism, when present, may be configured to bias the torque-adjusting drum to an adjustment position, and thus away from a/all retained position(s). In such a configuration, the biasing mechanism may be described as providing a disengagement force that must be removed or overcome to configure/retain the torque-adjusting drum in a selected retained position. As a further example, the biasing mechanism optionally may bias/urge (and/or impart forces that bias/urge) the torque-adjusting drum away from the base of the bracket assembly and/or a tooth to which the base is mounted. As yet another example, the biasing mechanism optionally may bias/urge (and/or impart forces that bias/urge) the torque-adjusting drum toward the base of the bracket assembly and/or a tooth to which the base is mounted. As still further examples, the biasing mechanism optionally may bias/urge and/or exert forces that bias/urge an archwire into/within or out of the archwire passage of the torque-adjusting drum.

Biasing mechanism 62, when present, may form a portion of positioning assembly 60. Biasing mechanism 62 additionally or alternatively may be a separate component of the bracket assembly and/or a portion of coupling mechanism 50, and/or subsequently discussed release mechanism 70, closure 100, and/or coupling mechanism 110. Biasing mechanism 62 may include any suitable type and/or number of components, or biasing members 63, that directly or indirectly provide the biasing, urging, and/or forces described herein. Examples of suitable biasing members 63, but are not limited to, springs, elastomeric members, and/or resilient members. In some embodiments, a biasing member 63 may interconnect and/or extend between at least two components of the bracket assembly. For example, a biasing member may interconnect the drum with the base and/or interconnect the drum with a closure of a self-ligating bracket assembly. In some embodiments, the biasing member may be secured to one component and may selectively engage and/or act upon another component. For example, a biasing member mat be secured to the base and selectively act upon the drum, may be secured to the drum and selectively act upon the base, may be secured to a closure of a self-ligating bracket assembly and selectively act upon the drum, etc.

When bracket assembly 10 and/or coupling mechanism 50 includes positioning assembly 60, the bracket assembly, coupling mechanism, and/or positioning assembly optionally also may include and/or interact with a release mechanism, or clutch, 70. Release mechanism 70, when actuated (or released, as the case may be), selectively disengages, frees, withdraws, and/or permits withdrawal of, the positioning assembly to an unlocked, or unactuated, position so as to enable repositioning of the drum relative to the base. Expressed in slightly different terms, the release mechanism, when actuated, may disengage the positioning assembly, overcome the retaining forces imparted by positioning assembly 60 and/or biasing mechanism 62, and/or otherwise permit the drum to be moved from a retained position to an adjustment position and then further moved to a different retained position. Upon release, or deactuation, of the release mechanism (or re-engagement of the clutch, as the case may be), the positioning assembly again operatively engages the drum to retain the drum in the newly selected retained position.

Actuation of the release mechanism may occur by any suitable mechanism, or actuator. Examples include, but are not limited to, levers, switches, buttons, slides, repositionable gears, force-receiving members, tool receivers, etc. Release mechanism 70, when utilized, may be configured to be actuated by any suitable mechanism or force, with an example being the direct or indirect application of external force to the release mechanism to actuate the release mechanism and thereby configure the positioning assembly to an unactuated, or unlocked, position. As an additional example, release mechanism 70, when utilized, may be configured to and/or to be actuated by the receipt of a force sufficient to disengage or overcome forces exerted by a biasing mechanism 62 to retain the torque-adjusting drum in a retained position.

As an example, the bracket assembly may be configured such that the application of external force to the drum and/or a region of the external surface of the base will transmit this force to actuate the release mechanism, such as via a lever, slide, switch, plunger, or similar mechanism incorporated into the bracket assembly. In some embodiments, this force may be an axial force that is toward or away from the tooth to which the base is mounted, and in some embodiments this force may be and/or include a pivotal or rotational force that is imparted to the drum, release mechanism, or other portion of the bracket assembly to actuate the release mechanism.

As another example, the bracket assembly optionally may include a socket, or receiver, 80 that is configured to selectively receive at least a tip 82 of an adjustment tool, or actuator, 84 that is sized to permit an operator, such as an orthodontist or technician, to apply the necessary force to actuate and/or release the release mechanism. In FIG. 1, dash-double-dot lines are utilized to schematically depict that the depth of receiver 80, when present, may vary without departing from the scope of the present disclosure.

For example, in some embodiments, the receiver may simply extend into the body of the drum, such as to provide a seat, or socket, for the tip of the tool to be inserted before the tool is urged axially (or in any other suitable direction) to reposition the drum to a different selected position. Although not required, in such an embodiment, the release mechanism may be designed to be released by forces that urge the drum generally toward the tooth to which the bracket is mounted.

As a further example, the receiver may extend sufficiently into the drum and/or at a suitable orientation within the drum to permit receipt of a tip 82 that has a lateral projection, adjustable width or cross-section, and/or otherwise is configured to be selectively secured in contact with the drum. In such a configuration, once the tip is secured in contact with the drum, the user may actuate the release mechanism, and thereby release the drum to be repositioned to a different retained position, by pulling axially on the tool to thereby urge the drum away from the tooth. This movement of the drum disengages and/or otherwise frees the drum from the retention provided by the positioning assembly so that the drum may be rotated to a new orientation, such as by the user pivoting the tool while the drum is in this adjustment position. Although not required, in such an embodiment, the drum may be biased to return toward the tooth, and thus to a retained position, so that release of the user-imparted upward/disengagement force on the drum permits the drum to automatically return to a retained position.

In a further example, the receiver may extend through the drum, such as to permit tip 82 of the tool to engage, and thereby actuate or release a release mechanism 70 that is positioned beneath the drum, such as between the drum and a portion of the base that is proximate tooth 14. Although not required, in such an embodiment, the user may insert the tool into the receiver and urge the tool axially toward the tooth until the release mechanism is engaged and actuated to permit relative rotation of the drum. Furthermore, pivotal/rotational movement of the tool within the receiver once inserted therein may impart forces to the drum to reposition the drum to a new retained position. Upon release of the axial force on the tool toward the tooth, the positioning assembly may automatically re-engage the drum and/or a biasing mechanism may automatically urge the drum back into a retained position.

Receiver 80 thus is illustrated schematically in FIG. 1, and when present, may have a variety of sizes, orientations, and/or depths. Receiver 80 optionally may extend into and/or through the archwire slot, may form a portion of the archwire slot, and/or may be defined by the archwire slot.

A potential benefit of having such a selectively actuated release mechanism is that the tool may be suitably sized for handling and positioning by the user to actuate (or release) the release mechanism and/or otherwise transmit desired forces to the bracket assembly and/or components thereof, despite the small size of the bracket assembly. Furthermore, while not required to all embodiments, bracket assembly 10 additionally or alternatively may be configured so that the tool, when operatively received into receiver 80, may be utilized by the user to adjust the relative rotation of the drum relative to the base. In some such embodiments, the tool and/or bracket assembly may include a scale, gradations, or other visual indicia 86 to indicate to the user the relative rotational position of the drum relative to the base. Indicia 86 is schematically illustrated in FIG. 1 and is intended to refer to a series of grooves, scores, hash marks, numbers, gradations, or similar markings that graphically indicate this relative rotational position to the user.

A further option for bracket assemblies 10 with receiver 80 and tool 84 is the ability for a user to adjust at least the torque to be applied by the bracket assembly (during prescriptive use thereof) while archwire 20 is operatively positioned within archwire slot 18 (i.e., without requiring removal of the archwire (or other component parts of the bracket assembly) to make the desired adjustment. It is within the scope of the present disclosure that any of the disclosed bracket assemblies may enable adjustment of the to-be-applied torque, via selective relative rotation of drum 16, without requiring removal of an archwire that is operatively positioned within the bracket's archwire slot. It is certainly an option for the user to remove and/or replace the archwire, depending on the user's preferences and/or the patient's needs, but removal may not be required simply due to the desire to adjust the relative rotation of the drum, and thereby the to-be-applied torque.

Although not required to all bracket assemblies 10 according to the present disclosure, some bracket assemblies 10 according to the present disclosure may be a conventional, or "ligating" bracket assembly 11 that requires a ligature or other separate retainer to be used to secure the archwire within archwire slot 18. As discussed, the schematically illustrated base 12 of FIGS. 1 and 2 optionally may include any suitable type, shape, and/or number of tie wings or other suitable structures for securing a ligature to retain the archwire in the archwire slot for prescriptive use of the bracket assembly. However, it also is within the scope of the present disclosure that some bracket assemblies 10 according to the present disclosure are self-ligating bracket assemblies 13. Accordingly, in such embodiments, the bracket assemblies are designed and shaped so that the archwire is received and retained in the archwire slot without requiring the use of separate ligating bands or wires.

Accordingly, when in use to apply corrective forces to a patient's tooth, self-ligating bracket assemblies 13 define a closed boundary around an archwire that is properly inserted into the archwire slot. By "closed boundary," it is meant that the archwire slot defined by the bracket assembly bounds, or surrounds, an archwire (as considered from the perspective of a plane that is transverse to the longitudinal axis of the archwire and/or the archwire slot) that is received through the archwire slot such that the archwire cannot be removed from the archwire slot other than by sliding the archwire in a longitudinal, or axial, direction, as measured relative to the archwire. In other words, the self-ligating bracket assembly defines an opening (typically extending generally parallel to the base, or body, of the bracket assembly) into which an archwire may be inserted and removed from the archwire slot, with a self-ligating bracket assembly further including a closure to selectively obstruct this opening. When in use to apply corrective forces to a patient's tooth, self-ligating bracket assemblies 13 form an archwire slot that does not provide an opening of sufficient size for the archwire to be removed from the archwire slot by translating or otherwise moving the archwire in a lateral, or transverse, direction measured with respect to the archwire slot.

Self-ligating bracket assemblies 13 according to the present disclosure may be selectively configured between an open, or installation, configuration and a closed, or corrective, configuration. A closed configuration refers to when the closure and base of an installed bracket assembly are operatively coupled together to receive and retain an archwire within the archwire passage, and thereby to transmit corrective forces to the patient's tooth. When the archwire is positioned within the archwire slot of a self-ligating bracket assembly 13 that is in a closed configuration, the archwire is retained within the archwire slot, which as discussed, defines a closed boundary (measured transverse to the axis of the portion of the archwire received within the archwire passage and/or the transverse axis of the archwire passage) around the archwire. In this closed configuration, the archwire optionally also may be at least frictionally retained against longitudinal, or axial, movement relative to the archwire passage, but the bracket assembly does not provide a physical barrier against longitudinal movement of the archwire relative to the archwire passage. In contrast, in the open configuration, at least a portion of the closure is moved relative to the base to permit removal of the archwire from the archwire passage in a direction other than in an axial, or longitudinal direction (measured relative to the axis of the portion of the archwire that is received within the archwire passage), such as through an opening in the archwire passage that is not obstructed when the closure is moved to the open configuration. In other words, in the open configuration, an archwire may be inserted into and/or removed from the archwire passage, such as in a translational direction measured relative to the base of the bracket assembly, and/or by respectively moving the archwire toward or away from the tooth to which the base of the bracket assembly is secured. In the open configuration, the archwire passage of the bracket assembly does not define a closed boundary around the portion of an archwire received therein (as measured transverse to the longitudinal axis of the archwire and/or archwire passage), thereby providing an opening or slot through which the archwire may be inserted into and/or removed from the archwire passage.

Closure 100 is coupled, and in some embodiments removably coupled, to base 12 by at least one connecting assembly 110, which provides for at least one of pivotal, releasable, and/or separable coupling of the closure to the base. As used herein, a connecting assembly that is configured to provide releasable, or removable, coupling between the closure and the base refers to a connecting assembly that is designed, or constructed, to provide for repeated engagement and disengagement of the corresponding portions of the coupling assembly, the closure, and/or the base without destruction of the closure, the base, or the connecting assembly. As further used herein, this selective releasing of the closure from the base means that at least the portion of the closure that was coupled to the base by the connecting assembly may be selectively pivoted or otherwise moved away from the corresponding portion of the base, such as to configure the bracket assembly from its closed configuration to its open configuration and thereby permit the insertion of an archwire into the archwire passage or the removal of an archwire from the archwire passage. In some embodiments, the one or more connecting assemblies 110 may provide for partial and/or complete separation of the closure from the base, with partial separation referring to a portion of the closure pivoting or otherwise moving away from the base while another portion of the closure remains connected to the base. In contrast, complete separation of the closure from the base refers to the entirety of the closure being removed, and thus being spaced apart and/or disconnected, from the base.

A connecting assembly 110 additionally or alternatively may be referred to as a latch and/or a coupler, and may include any suitable structure that provides for the selective coupling of the closure and the base. In at least FIG. 1, connecting assembly 110 is depicted with a dashed box to schematically represent that the shape, size, components, and number of connecting assemblies may vary without departing from the scope of the present disclosure. A connecting assembly may include a portion that is attached to, permanently attached to, or even integrally formed with at least a portion of the closure and/or the base, and the connecting assembly may include any suitable number of components, or portions, to provide for the selective coupling of the base and the closure.

When the bracket assembly is in the open configuration, a connecting assembly may (but is not required in all embodiments to) include a portion that is connected to the closure and a separate portion that is connected to the base, with these portions being interconnected when the bracket assembly is reconfigured to its closed configuration. Connecting assembly 110 may be configured to allow closure 100 to release from base 12 responsive to an external force that is applied to self-ligating bracket assembly 13 and without damaging or destroying the connecting assembly, the closure, or the base. Connecting assembly 110 may include one or more of a hinge, clasp, and/or other fastening structures and optionally may further include resilient structures placed between base 12 and closure 100 to dampen external forces applied to the bracket assembly and/or to lock the closure and/or fastening structures in a closed configuration.

As a further optional feature, when bracket assembly 10 is a self-ligating bracket assembly 13, as discussed herein, tool 84 may be selectively utilized to release the connecting assembly 110 to permit the closure, or gate, 100 of the self-ligating bracket assembly to be moved from a closed configuration, in which the inlet 46 of the archwire slot is obstructed, to an open configuration, in which an archwire may be selectively inserted into and/or removed from the archwire slot via inlet 46. As also indicated schematically in FIGS. 1 and 2 at 112, when bracket assembly 12 includes a closure 100 and a receiver 80, the closure may include a closure passage, or closure socket, that is sized to permit at least tip 82 of tool 84 to be inserted past/through the closure to be operatively inserted or otherwise received into the receiver, as discussed herein.

Bracket assemblies 10 according to the present disclosure, including bracket assemblies 11 and/or 13, optionally may include an archwire positioning structure, or archwire positioning mechanism, 92, which is schematically illustrated in FIG. 1. Archwire positioning mechanism 92 is configured to urge the archwire in a selected direction and/or to a selected position within the archwire slot. As an example, the archwire positioning mechanism, when present, may be configured to urge the archwire away from inlet 46 and/or toward one of the walls 90 of the archwire slot (such as the wall distal inlet 46). Examples of a suitable component of, and/or structure for, archwire positioning mechanism 92 include one or more spring, elastomer, resilient material, and/or compliant material. In some embodiments, archwire positioning mechanism 92, when present, additionally or alternatively may be a biasing member 63 of a biasing mechanism 62.

When bracket assembly 10 is not a self-ligating bracket assembly, the archwire positioning mechanism may extend into the archwire slot from one of the walls of the archwire slot, from face 40 of the drum, and/or from the base. When bracket assembly 10 is a self-ligating bracket assembly that includes archwire positioning mechanism 92, the above examples of suitable configurations may be utilized. Additionally or alternatively, the archwire positioning mechanism may be coupled to closure 100. It also is within the scope of the present disclosure that archwire positioning mechanism 92 may be used to adjust the configuration and/or to-be-applied forces of other bracket assemblies other than bracket assemblies 10.

The location of archwire slot 18 may vary from the locations that are illustrated schematically in FIGS. 1 and 2. As an example, when bracket assembly 10 is a self-ligating bracket assembly 13, the drum may be selectively coupled (and selectively rotatable relative thereto) to the base or to the ligating gate, or closure, that pivots, translates, or otherwise moves relative to the base to selectively obstruct or permit access to the archwire slot. In embodiments in which the drum is coupled to the self-ligating closure, it follows that the archwire slot may have an inlet, or opening, that generally faces the patient's tooth, as indicated in dashed lines in FIG. 1. In contrast, when the drum is coupled to the base, the archwire slot typically will include an inlet, or opening, that generally faces away from the tooth.

While a suitable configuration for archwire slot 18 is to have a rectilinear cross-sectional configuration (measured transverse to the long axis of the slot), as discussed, other shapes and/or configurations may be utilized. As an example, in some embodiments, it may be desirable for at least one wall 90 (and optionally at least two or at least three walls) of the archwire slot (and thus of the drum) to have a non-planar configuration that permits archwire 20 to be operatively received within the slot in more than one relative orientation, such as depending upon the portion(s) of the non-planar wall that are engaged by the archwire. Such a non-planar configuration is illustrated schematically at 94 in FIG. 1, with one of walls 90 shown with a projection, or "hump" that extends into the archwire slot. Additional examples of suitable configurations for non-planar archwire slot walls are disclosed in U.S. Patent Application Publication No. 2011/0183280, which is incorporated herein by reference.

While many of the components of bracket assembly 10 are separately and/or individually described herein, it is within the scope of the present disclosure that two or more such components may be embodied and/or implemented together, may share one or more structural elements, and/or may form a subassembly of the bracket assembly. For example, release mechanism 70, when present, optionally may include and/or be utilized with a biasing mechanism 62 that urges the drum into or out of engagement with the positioning assembly. Likewise, positioning assembly 60 may include and/or be utilized with a biasing mechanism that selectively urges the drum into or out of engagement with the positioning assembly. As a further example, coupling mechanism 50 and positioning assembly 60 may share one or more structural portions of the bracket assembly to selectively define a rotational path of movement of the drum relative to the base and to selectively retain the drum in a selected, and optionally predefined, retained position. When bracket assembly 10 is a self-ligating bracket assembly 13, closure 100 optionally may include and/or be configured for movement relative to base 12 with at least a portion of the drum, positioning assembly, coupling mechanism, and/or release mechanism.

Additional, less schematic, examples of bracket assemblies 10 according to the present disclosure, as well as tools 84 for use therewith, are disclosed in FIGS. 3-6 and 8-15. These additional examples include (1) a bracket assembly 10 in the form of a self-ligating bracket assembly 13 that is shown in FIGS. 3-6 and generally indicated at 200, (2) a bracket assembly 10 in the form of another self-ligating bracket assembly 13 that is shown in FIGS. 8-9 and generally indicated at 300, (3) a tool 84 that is configured for use with bracket assembly 200 or bracket assembly 300 and which is shown in FIG. 10 and generally indicated at 400, (4) a bracket assembly 10 in the form of another self-ligating bracket assembly 13 that is shown in FIG. 11 and generally indicated at 500, and (5) a bracket assembly 10 in the form of another self-ligating bracket assembly 13 that is shown in FIGS. 12-15 and generally indicated at 600.

Unless otherwise indicated, the reference numerals, variants, and options that were introduced in the preceding discussion of bracket assemblies 10 and tool 84 in connection with FIGS. 1 and/or 2 are applicable to bracket assemblies 200, 300, 500, and 600, as well as to tool 400. Accordingly, the same reference numerals will be utilized in many of FIGS. 3-15, and for the sake of brevity, not every element, component, example, variant, option, etc. will be discussed again in connection with bracket assemblies 200, 300, 500, and 600, or tool 400, and not every applicable reference numeral will be utilized in each of FIGS. 3-15. However, it is within the scope of the present disclosure that unless otherwise indicated, the previously discussed elements, components, examples, variants, options, etc. may be utilized with the subsequently discussed bracket assemblies and tool. Thus, bracket assemblies 200, 300, 500, and 600 illustrate additional examples of bases 12, torque-adjusting drums 16, coupling mechanisms 50, positioning assemblies 60, biasing mechanisms 62, release mechanisms 70, receivers 80, closures 100, and/or connecting assemblies 110.

In FIGS. 3-6, collectively, bracket assembly 200 is a self-ligating bracket assembly 13 that includes a rotatable torque-adjusting drum 16 that selectively receives an archwire 20 within an archwire slot 18 that is defined by, or within, the drum. The drum is selectively rotated within a range of positions relative to base 12, and thus relative to a tooth to which the bracket assembly is mounted. This rotation alters the relative rotational orientation of the archwire relative to the base and/or tooth, thereby altering the prescriptive forces that are imparted to the tooth during prescriptive use of the bracket assembly.

Figure 4:
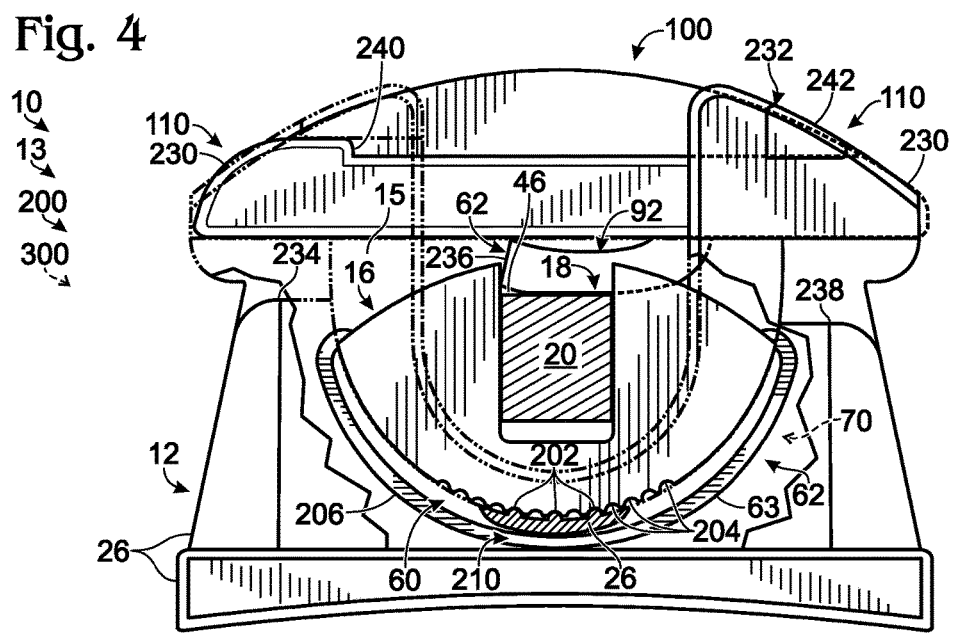
FIG. 4 is a side elevation view of the bracket assembly of FIG. 3 with the closure of the bracket in a closed configuration and the torque-adjusting drum in a retained position.
Figure 5:
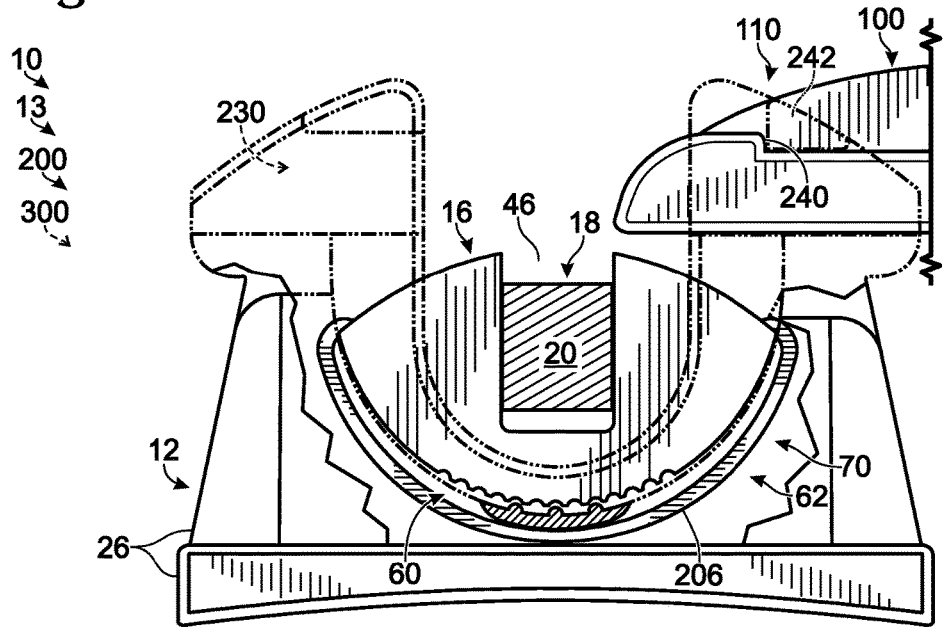
FIG. 5 is a fragmentary side elevation view of the bracket assembly of FIG. 3 with the closure in an open configuration and the torque-adjusting drum in an adjustment position.

In FIG. 3, bracket assembly 200 is shown in an exploded view that may permit easier viewing of the components of the bracket assembly. In FIG. 4, the bracket assembly is shown in an assembled state in which an archwire is received and retained in the archwire slot of the torque-adjusting drum 16. In FIG. 4, the drum is in a selected retained position of the plurality of defined retained positions within the rotational range of positions of the drum, and the closure of the bracket assembly is in a closed configuration, in which the closure restricts removal of the archwire through the inlet 46 of the archwire slot. In FIG. 5, the bracket assembly is shown with the closure in an open configuration, in which an archwire may be removed from the archwire slot via the inlet of the archwire slot due to the closure not obstructing the inlet of the archwire slot. In FIG. 5, the torque-adjusting drum is shown in an adjustment position, in which the drum is free or otherwise permitted and/or not obstructed or restricted from being selectively rotated within the defined range of positions, such as to a different retained position. In FIG. 6, the bracket assembly is again shown with closure 100 in a closed configuration and in which the torque-adjusting drum is positioned in a retained position that is different from the retained position of FIG. 4. Accordingly, due to this repositioning of the torque-adjusting drum, and thus repositioning of the archwire within the drum's archwire slot, different prescriptive forces are imparted to a tooth to which the bracket assembly is mounted during orthodontic use of the bracket assembly.

In FIGS. 3-6, closure 100 is illustrated as moving between its open and closed configurations by translating, or sliding, relative to the base of the bracket assembly. As discussed, other motions may be used, such as pivotal movement of the closure relative to the base. In the illustrated example, bracket assembly 200 includes a connecting assembly 110 that defines the path of travel of the closure and which restricts unintentional removal, or detachment, of the closure from the base. Connecting assembly 110 includes both closure guides 230 that are formed in the base, and a pair of closure stops 232 that restrict detachment of the closure from the base. As perhaps best seen in FIG. 4, closure 100 includes a spring member 220 that projects from the closure into the enclosure 15 of the base (at least when the closure is in the closed configuration). The shape and orientation of the spring member enables the closure to be installed on and/or coupled to, the base by inserting the closure into the closure guides 230 from the left side of the bracket assembly of FIG. 4. When this occurs, spring member 220 will deflect over end wall 234 of the base to permit the spring member to pass into the enclosure defined by the base. However, reverse movement of the closure to detach the closure from the base is restricted because the end 236 of the spring member will impact wall 234 instead of deflecting over the wall. Thus, the relative orientation of the spring member with respect to end wall 234 provides a closure stop 232. On the other hand, when the closure is translated to an open configuration, such as shown in FIG. 5, spring member 220 does not prevent this movement because the opposed end wall 238 is lower than end wall 234. Detachment of the closure from the base when the closure is moved to the open configuration is prevented because a shoulder 240 of the closure engages a projection, or obstruction, 242 along the path defined by closure guides 230, as indicated in FIG. 5, to provide a closure stop 232 on that end of the path.

Spring member 220 also may be utilized as an archwire positioning member 92, at least when the closure is in a closed configuration. As perhaps best seen in FIG. 4, spring member 220 projects away from the closure and extends against, or even at least partially into, the archwire slot. In this position, the spring member at least restricts removal of an archwire that is within the archwire passage through inlet 46 of the archwire passage. The spring member additionally may urge, or bias, the spring member into, or further into, the archwire passage.

As perhaps best seen in FIGS. 3 and 4 and as indicated in FIG. 3, bracket assembly 200 utilizes a base 12 that defines an arcuate track, or drum-engagement surface, 48 that cooperates with a corresponding arcuate base-engagement surface 42 of torque-adjusting drum 16 to define rotational coupling mechanism 50. The portions of the drum and the base that define the engagement surfaces 42, 48 and guide the rotational path of movement of the drum may be referred to as coupling members 52 of the coupling mechanism, as indicated in FIG. 3.

The torque-adjusting drum is selectively rotated within the range of rotational positions within the enclosure 15 defined by the base, with this range of positions defining a plurality of spaced-apart retained positions. In the illustrated embodiment, the drum is selectively retained with a range of rotational positions relative to the base, such as in a selected one of a plurality of predefined spaced-apart retained positions defined by the selective engagement of gear tabs 202 by gear slots 204. Gear tabs 202 and gear slots 204 thus may be described as forming at least a portion of a positioning assembly 60. Gear tabs 202 may additionally or alternatively be referred to as a plurality of spaced-apart ribs, projecting members, etc., and gear slots 204 may additionally or alternatively be referred to as a plurality of spaced-apart recesses, notches, detents, etc. As illustrated, the gear tabs are formed on and/or extend from a member 26 of the base 12, and the gear slots extend into and/or are formed in torque-adjusting drum 16. In the illustrated example, three radially spaced-apart gear tabs and a greater number of incrementally spaced-apart gear slots are utilized. As discussed, the position of these components may be reversed, and a greater or lesser number of either/both of the gear tabs and gear slots may be utilized so long as there is at least one gear tab and at least a plurality of gear slots or other suitably sized and positioned recesses to define a corresponding plurality of retained positions for the torque-adjusting drum.

When at least one gear tab 202 is received into a gear slot 204, the drum may be described as being in a retained position, as further relative rotation of the drum relative to the base (and thus further adjustment of the prescriptive forces to be imparted to a tooth during prescriptive use of the bracket assembly) is restricted until the drum is moved to an adjustment position, in which the gear tabs do not extend into the gear slots.

Bracket assembly 200 provides two illustrative examples of biasing mechanisms 62 and corresponding biasing members 63. Specifically, and as indicated in FIGS. 3 and 4, the bracket assembly includes springs, or spring members, 206 and 220. Spring member 206 couples the drum to the base and thereby prevents removal of the drum from the enclosure 15 of the base. Spring member 220 projects from closure 100 and selectively engages an upper surface of the drum to urge the drum toward a retained position when the closure is in a closed configuration. Spring members 206 and 220 additionally or alternatively collectively may be referred to as forming biasing mechanism 62, as opposed to being described as providing two biasing mechanisms 62. It also is within the scope of the present disclosure, as discussed, that only one of the spring members may be present in a particular embodiment and/or that a different style of spring member, resilient member, elastomeric member, etc. may be utilized to provide the biasing forces.

As perhaps best seen in FIG. 4, spring member 206 extends from the drum, through a passage 210 in the base, and back to the drum to define a closed loop, or closed perimeter, around the portion of the base that includes gear tabs 202. Spring member 206 thus may be referred to as a drum-retaining spring member. Depending on its construction and/or implementation, spring member 206 may be configured to bias or otherwise urge the drum to an adjustment position (and thus away from a retained position) or to bias or otherwise urge the drum into (and/or to stay within) a retained position. For example, spring member 206 may be configured to exert forces on the drum to push the drum away from tabs 202 or to draw the drum against the tabs.

When spring member 206 is configured to urge the drum to a retained position, then spring member 206 additionally or alternatively may be described as forming a portion of positioning assembly 60, as the spring member assists in retaining the drum in a selected retained configuration. Accordingly, a suitable release mechanism will either disengage the force that the spring member is exerting on the drum, or more likely, will urge the drum away from the retained position with a greater force than the retaining force applied by the spring member. For example, and as discussed, a tool may be coupled to the drum and/or inserted under/through the drum to enable such a force to be applied to the drum.

When spring member 206 is configured to urge the drum to an adjustment position (i.e., away from a retained position), then the spring member additionally or alternatively may be described as forming a portion of release mechanism 70. Specifically, when the spring member moves the drum from a retained position to an adjustment position, it releases the drum to be repositioned to a new retained position. In slightly different terms, the drum is removed from the retained position defined by the inter-engagement of the gear tab(s) and gear slot(s). FIG. 5 illustrates an example of spring member 206 functioning as a release mechanism 70. As shown, the closure 100 of the bracket assembly is moved to an open configuration, in which an archwire 20 may be selectively inserted into or removed from archwire slot 18 through inlet 46 of the archwire slot. As also shown in FIG. 5, spring member 206 has moved the drum away from the base a sufficient distance for the gear tabs to be withdrawn from the gear slots (i.e., to a position in which the positioning assembly has been released or disengaged). From this position the drum may be selectively rotated to a different rotational orientation relative to the base, such as for securement in a new retained position that defines a different prescriptive force during use of the bracket assembly. When the closure is returned to a closed configuration, such as shown in FIG. 6, spring member 220 may urge the drum into the selected retained position, with spring member 220 thereby functioning as at least a portion of positioning assembly 70.

As discussed, torque-adjusting drum 16 optionally may include at least one receiver 80 that is sized and positioned to receive an adjustment tool, such as the tip of an adjustment tool, through which a user may impart forces to the drum and/or other portion of the bracket assembly. For example, these forces may urge the drum to or away from a retained position and/or an adjustment position, may engage a positioning assembly, may actuate a release mechanism, etc.

FIG. 7 provides graphical, somewhat schematic, examples of suitable configurations for receivers 80 and/or torque-adjusting drums 16 that may be used with bracket assemblies 10 according to the present disclosure. In the left portion of FIG. 7, drum 16 includes a receiver 80 in the form of a socket, or closed-ended bore, 140 that extends into the body of the drum but not through the body of the drum. Socket 140 is sized to permit the tip of an adjustment tool, such as a probe, a scaler, or a specialized tool, to be received and/or seated into the socket to provide a stable connection through which a user, such as an orthodontist or technician, may apply forces to the drum through the tool. With the socket that is illustrated in solid lines, these forces typically will be or will include axial forces that urge the drum toward the base, the tooth to which the bracket assembly is mounted, and/or toward a retained position. As indicated in dashed lines in the left portion of FIG. 7, socket 140 optionally may include a flared or expanded region 142 that extends within the body of the drum. In such a configuration, the tool may include an elbow or transversely extending/extendable portion that may be selectively extended into region 142 to permit the user to use the tool to pull or otherwise urge the drum away from the housing, tooth, and/or retained position.

In the central portion of the drum of FIG. 7, two additional examples of suitable receivers 80 are illustrated. A first example is that archwire slot 18 may itself form a receiver 80 into which a portion of a tool is inserted to convey adjustment, actuating, positioning, or other forces to the bracket assembly. Archwire slot 18 optionally may include a flared or expanded region 142, which may provide a form of receiver that is better suited to receive user inputs that urge the drum away from a retained position.

In the right portion of the drum of FIG. 7, an example of a receiver 80 in the form of an aperture, passage, or open-ended bore 144 that extends entirely through the body of the torque-adjusting drum is shown. Such a receiver may be useful, for example, to permit the tool to extend through the drum to engage the lower surface of the drum and to permit the drum to be pulled or otherwise urged away from the retained position, tool, etc. Additionally or alternatively, such an example of a receiver 80 may be useful to permit the user to apply force to and/or otherwise actuate portions of the bracket assembly that are beneath the drum. For example, a positioning assembly, biasing mechanism, and/or release mechanism may be so positioned and thereby actuated by user inputs that are received through aperture 144.

In the left and right portions of the torque-adjusting drum 16 of FIG. 7, reference numerals 146 designate recesses (which may be interconnected to form a bore or channel that extends through the drum) into which portions of spring 206 extend to couple the spring to the drum. However, it is within the scope of the present disclosure that the shape and/or size of the recesses and/or spring may be selected to permit recesses 146 to selectively receive portions of an adjustment tool to couple the tool to the drum to assist a user to apply desired forces to the drum, such as to reposition the drum relative to the base of the bracket assembly.

FIGS. 8 and 9 collectively provide another example of a bracket assembly 10 in the form of a self-ligating bracket assembly 13 that is indicated generally at 300. Specifically, FIG. 8 illustrates another example of a suitable closure 100, and FIG. 9 illustrates other examples of a base 12, torque-adjusting drum 16, coupling mechanism 50, positioning assembly 60, biasing mechanism 62, and receiver 80. In FIG. 9, only a portion of the base is illustrated, and it should be understood that a complimentary and/or mirror-image second half would be present in a fully assembled base 12 for bracket assembly 300. When the base is formed from at least these two base members 26, the members may be secured together via any suitable mechanism or process. In FIGS. 8-9, reference numeral 200 is indicated in dashed lines in addition to reference numeral 300 being indicated in solid lines; and reference numeral 300 is indicated in dashed lines in FIGS. 4-5 in addition to reference numeral 200 being indicated in solid lines. This is intended to graphically represent that the base of FIG. 9 optionally may be used with the closure of FIGS. 3-6 and that the base of FIGS. 3-6 optionally may be used with the closure of FIG. 8. Other selective utilization of features, components, variants, etc. of the various bracket assemblies 10 disclosed herein also is within the scope of the present disclosure.

In FIG. 8, closure 100 is very similar to the closure of bracket assembly 200 of FIGS. 3-6, except that the closure of FIG. 8 includes a drum-engaging member 320 instead of the spring member 220 of FIGS. 3-6. Drum-engaging member 320 may provide the same or similar biasing and/or positioning functions as spring member 220. As illustrated, member 320 extends from spaced-apart regions of the underside of closure 100 to define an arch 322 having a peak 324 that is generally positioned to align with the archwire slot of the bracket assembly's drum, at least when the closure is in the closed configuration. Drum-engaging member 320 may be a spring, or spring member, but it optionally may be formed from a resilient material that has the illustrated uncompressed, or nominal, shape.

In FIG. 9, base 12 includes projections 340 that are received into corresponding channels 342 in drum 16. In this illustrated example, projections 340 extend generally parallel to the axis of rotation of the drum. As drum 16 rotates within its range of rotational positions, projections 340 may form a portion of coupling mechanism 50 to guide the path of the drum and/or may function as stops 54 to limit the rotational path of the drum relative to the base. Also shown in FIG. 9 is a biasing mechanism 62 in the form of a flexible, compliant, and/or resilient member 350 that is positioned beneath drum 16 and which includes gear tabs 202 of a positioning assembly 60. Gear tabs 202 are selectively received into gear notches 204 on the drum to retain the drum in a retained position. This member 350 normally is engaged with the drum to retain the drum in a retained position. To adjust the position of the drum to a different retained position, member 350 needs to be urged sufficiently away from engagement with the drum to withdraw gear tabs 202 from the corresponding gear notches 204. For example, a tool or other suitably shaped member may be inserted through either or both of the receivers 80 in the drum. Receivers 80 may be described as extending through the drum and/or as being recesses, or waists, that are formed in the drum. Regardless, the receivers provide a passage through which a rod or similar tool may be inserted past the drum and into engagement with member 350 to impart sufficient pressure on member 350 to deflect the member away from the drum so that the drum is released to be rotated to a new position. Upon release of the user-applied force to member 350, member 350 will automatically re-engage the drum to retain the drum in a retained position.

FIG. 10 provides an example of a tool 84 that may be utilized with some bracket assemblies 10 according to the present disclosure, including bracket assemblies 200 and 300, to selectively adjust at least the relative rotation of drum 16 relative to base 12, and thereby the amount of to-be-applied torque. The tool 84 of FIG. 10 is indicated generally at 400 and is configured for use with bracket assemblies 200 and 300. As shown, tool 400 includes a tip 82 that is adapted to be selectively received into a socket, or receiver 80 of the bracket assembly. As illustrated, archwire slot 18 is used as the receiver, although this is not required to all embodiments. However, it is within the scope of the preceding discussion of bracket assemblies 10 that archwire slot 18 is itself an example of a suitable receiver. A potential benefit of using the archwire slot as the receiver, although not required, is that any indicia or other rotation/torque scale may be more easily calibrated and/or aligned with the actual angular orientation of the drum and relative to the base. As indicated in dashed lines at 20, tool 400 optionally may be utilized to adjust the orientation of the drum without requiring removal of archwire 20 from the archwire passage. For example, and perhaps depending upon the size/shape of the archwire being utilized, the archwire passage may have sufficient size and/or clearance for receipt of tip 82 while the archwire is within the archwire passage.

Also shown in FIG. 10 is an optional accessory for tool 400, namely, visual gauge, or measurement device 410 that includes the previously discussed graphical indicia 86 to present to a user the relative rotation of the drum relative to the base, and thus relative to a corresponding tooth. In the depicted embodiment, a series of spaced apart grooves 412 are utilized to indicate incremental changes in the relative rotation, and thus the to-be-applied torque. Any of the illustrative examples of suitable spacing and/or intervals between the grooves may be utilized. Also, an optional tab, or finger, 414 that may be selectively received into the notches is shown. When present, finger 414 may be formed from a resilient or flexible material, and optionally may be designed to emit an audible and/or tactile signal as the finger is inserted into and/or removed from the grooves. It is within the scope of the present disclosure that other indicators or indicia, including numerical indicia, may be utilized in addition to, or in place of, grooves 412. As shown, measurement device 410 is sized to be supported and positioned directly on base 12 during use of tool 400.

FIG. 11 provides a further example of a bracket assembly 10 in the form of a self-ligating bracket assembly 13, with the specific example being indicated generally at 500. Bracket assembly 500 is functionally very similar to bracket assembly 200, and in this regard provides a further example of a bracket assembly 10 in which the torque-adjusting drum is coupled to the base of the bracket assembly by a biasing mechanism 62, such as spring member 206. Thus, the selective rotational positioning of drum 16 relative to base 12 and within the range of rotational positions to selected retained positions is analogous to the preceding description of bracket assemblies 10 (generally) and 200 (more specifically).

In contrast to the previously illustrated bracket assemblies, bracket assembly 500 includes a closure 100 that is coupled directly to torque-adjusting drum 16 instead of to base 12. Thus, connecting assembly 110 interconnects the drum and the closure, as opposed to the base and the closure, as in the examples of bracket assemblies 200 and 300. Thus, instead of base 12 defining closure guides 230, the drum does so. In the illustrated example, at least one of the closure stops 232, namely, a stop to restrict detachment of the closure as the closure is moved to its open configuration, also is defined by projection 242 of drum 16 obstructing the further movement of shoulder 240 of the closure. In such an embodiment, a closure stop 232 on the left side of the drum, as viewed in FIG. 11, may be provided by and/or on the corresponding portion of spring member 206, drum 16, and/or wall 510 of the base. It also is within the scope of the disclosure that the geometry of the closure guide, friction with the spring member and/or the closure guide, and/or an additional ligature may be utilized as a closure stop.

Although not required, coupling the closure directly to torque-adjusting drum 16 may permit the height (i.e., the distance that the bracket assembly projects away from the surface of a tooth to which the bracket assembly is mounted) to be reduced compared to a corresponding bracket assembly in which the closure is coupled directly to the base. Thus, such a bracket assembly may be referred to as a low-profile bracket assembly and/or a low-profile self-ligating bracket assembly.

FIG. 11 also illustrates that the end regions 207 of spring member 206 optionally may extend around, or on, the upper surface of the drum, as opposed to being received into slots in the arcuate lower/lateral surface of the drum. As a graphic reminder that the components, options, variants, etc. of other bracket assemblies 10 optionally may be utilized with other bracket assemblies that are disclosed herein, optional tie wings 520, archwire positioning mechanism 92 and receivers 80 are shown in dashed lines in FIG. 11.

FIGS. 12-15 provide a further example of a bracket assembly 10 in the form of a self-ligating bracket assembly 13, with the specific embodiment of FIGS. 12-15 being indicated generally at 600. Bracket assembly 600 provides a non-exclusive graphical illustration of a self-ligating bracket assembly in which closure 100 pivots relative to the base 12 of the bracket assembly between the previously discussed open and closed configurations. As indicated at 610 in FIGS. 12 and 13, the closure 100 is pivotally coupled to base 12 of the bracket assembly by a pivot 620. Pivot 620 may take any suitable form, such as a pivot pin, hinge, rotatable coupler, etc. This contrasts with the closure 100 of bracket assemblies 200, 300, and 500, which slide or translate relative to base 12.

As indicated in FIG. 12, bracket assembly 600 includes a connecting assembly 110 in the form of a biased connecting assembly 610. Biased connecting assembly 610 additionally or alternatively may be referred to as a pivotal connecting assembly 610 and/or a biased, pivotal connecting assembly 610. The biased connecting assembly selectively engages closure 100 to retain the closure in a closed configuration, in which archwire 20 may not be inserted into, or removed from, archwire slot 18 via inlet 46 of the archwire slot. Connecting assembly 610 includes a pivot, or hinge assembly, 620 that selectively couples the closure for pivotal movement relative to base 12 between a range of pivotal configurations that are bounded by a fully closed configuration and a fully open configuration. As used herein, an open configuration refers to a configuration in which an archwire may be inserted or removed from the archwire slot through the inlet of the slot, and thus there may be a range of open configurations. Similarly, a closed configuration may refer to any configuration of the closure in which there is insufficient clearance for an archwire to be inserted into or removed from the archwire slot through the inlet of the slot.

Connecting assembly 610 further includes a latch mechanism 630 that selectively retains the closure in a closed configuration and restricts pivoting the closure to an open configuration until the latch mechanism is disengaged from the closure. Additionally or alternatively, the connecting assembly may be described as being retained in the closed configuration by the latch mechanism 630 until the latch mechanism is pivoted or otherwise moved from the locked configuration shown in FIG. 12 to an unlocked configuration in which pivoting of the closure to an open configuration is no longer prevented by the latch mechanism. An example of such an unlocked configuration of the latch mechanism is illustrated in FIG. 13.

Latch mechanism 630 may take any suitable form and may have any suitable construction. One or both of pivot 620 and latch mechanism 630 may be biased, or spring biased, with a corresponding biasing mechanism urging the corresponding component to a particular configuration. For example, pivot 620 may be spring biased to urge the closure to an open configuration. In such an embodiment, configuring the latch mechanism to an unlocked configuration may cause the closure to automatically move, under the bias or force of the pivot's biasing mechanism, to or toward an open configuration. When biased, latch mechanism 630 typically will be biased to a locked configuration, or at least to the latch mechanism's position when the latch mechanism retains the closure in a closed configuration. In such a configuration, this biasing of the latch mechanism may assist in configuring the closure to its closed configuration and/or providing a restoring, or retaining, force that restricts unintentional opening of the closure. As discussed herein, when the closure 100 of bracket assembly 600 is in an open configuration, the corresponding torque-adjusting drum may be in an adjustment position. Accordingly, biasing mechanisms for the pivot and/or latch mechanism may be biasing mechanisms 62 for the drum and a corresponding positioning assembly 60 and/or release mechanism 70. Thus, in FIG. 12, the optional biasing mechanism for pivot 620 is indicated generally at 62 and more specifically at 622, and the optional biasing mechanism for latch mechanism 630 is indicated generally at 62 and more specifically at 632.

Latch mechanism 630 may be formed of any suitable material, with nickel titanium being an example of a suitable material. Although not required, the closure-engaging edges 634 of the latch mechanism may be chamfered or otherwise buffered to help facilitate a smooth movement of the closure into engagement with the latch mechanism, subsequent to displacement of the latch mechanism against its bias so that the closure may move to, or proximate, a closed configuration. This may result in return of the latch mechanism to or toward its locked configuration, where it now resists movement of the closure away from the closed configuration.

In some embodiments, base 12, closure 100, and/or latch mechanism 630 may be designed such that there is clearance between the underside 636 of the latch mechanism's head region (which as depicted has a T-shaped configuration) and the corresponding upper surface 638 of closure 100 when the closure is in the closed configuration. Specifically, by having this clearance, although not required, pressing/depressing the closure to this fully pivoted (closed) configuration may provide additional clearance to enable the latch mechanism to return fully to its biased position, and thereby more tightly or firmly secure the closure in the closed configuration.

In FIG. 13, the locked configuration of latch mechanism 630 is shown in solid lines, and an unlocked configuration of the latch mechanism is shown in dash-double-dot lines. Latch mechanism 630 may be selectively pivoted, slid, or otherwise moved between these configurations, such as responsive to user inputs thereto, to forces exerted by biasing mechanism 632, etc. As a further example, closure 100 of bracket assembly 600 includes a receiver 80 that is sized to receive at least the tip 82 of an adjustment tool 84. Once tip 82 is inserted into the receiver, the tool may be pivoted in the direction indicated in FIG. 13 with a large arrow (i.e., generally toward the latch mechanism and away from the archwire passage of the drum) to force the latch mechanism to pivot or otherwise move to an unlocked configuration. Thus, receiver 80 may be described as an open-sided receiver, or a notch, 680 that permits at least the tip of the tool to be inserted into the receiver, with this insertion proving a leverage point to use the tool to pry/force the latch mechanism to an unlocked configuration.

When pivot 620 is a biased pivot, this movement of the latch mechanism to an unlocked configuration may permit the closure to automatically pivot to, or at least toward, an open configuration, such as is shown in FIG. 14. As also perhaps best seen in FIG. 14, in the illustrated example, closure 100 includes at least one engagement surface 642 that extends at an oblique/inclined angle relative to an upper, or head, region 644 of the latch mechanism. As such pivoting of the closure toward its closed configuration, as indicated with an outline arrow in FIG. 14, causes engagement surface 642 of the closure to engage head 644 of the latch mechanism to force the latch mechanism to pivot or otherwise move to an unlocked configuration. Once the closure is pivoted to a closed configuration, and especially a fully closed configuration in which engagement surface 642 of the closure abuts a corresponding closure-engagement surface 646 of the base, the latch mechanism may be pivoted or otherwise moved back to its locked configuration. When the latch mechanism is a biased latch mechanism, this movement may be automatic, or at least automatically initiated, when upper surface 638 of closure 100 is beneath underside 636 of the latch mechanism.

Bracket assembly 600 provides a graphical illustration of a bracket assembly 10 in which drum 16 is rotationally coupled to closure 100 instead of base 12, with rotational coupling mechanism 50 thereby guiding the rotational movement of the drum against contact surfaces of the closure instead of contact surfaces of the base (as in bracket assemblies 200 and 300). Accordingly, relative rotation of torque-adjusting drum 16 within closure 100 is restricted when latch mechanism 630 retains the closure, and thus the bracket assembly, in a closed configuration. Similarly, release of the latch mechanism to permit the closure to pivot or otherwise move to an open configuration also enables relative rotational movement of the drum relative to closure 100, such as to a new selected retained position, and thereby relative to the base (when the bracket assembly is returned to a closed (operative) configuration).

As indicated in FIG. 13, bracket assembly 600 includes a coupling mechanism 50 that defines a range of rotational positions of drum 16, and thus archwire slot 18 relative to the closure, and thus relative to the base and any corresponding tooth to which the base is mounted. Drum 16 may be frictionally adjustable within an arguably infinite range of retained positions, such as depending upon a user exerting a sufficient force to cause relative rotation of the drum within the closure. In such an embodiment, the bracket assembly's positioning assembly may be the frictional and/or inter-engagement between drum 16 and closure 100.

In some embodiments, the bracket assembly may be configured to restrict adjustment of the drum between selected retained configurations when the closure is in a closed configuration, and thus when the latch mechanism secures the closure in this closed configuration. In such an embodiment, the latch mechanism also may be described as forming at least a portion of the bracket assembly's positioning assembly. Furthermore, tool 84 and receiver 680 may provide at least a portion of the bracket assembly's release mechanism to selectively disengage the forces applied to the closure by the latch mechanism so that the closure may be pivoted to an open configuration and thus so that the drum may be in an adjustment position. Once in such an adjustment position, drum 16 may be rotated relative to the closure to select a new retained position, into which the drum will be retained when the closure is resecured in a closed configuration, such as shown in FIG. 15.

In FIGS. 12 and 13, a further example of a receiver 80 is illustrated and is generally indicated at 682. Receiver 682 receives a tip 82 of a tool 84 (as indicated in dashed lines in FIG. 13) to provide a mechanism to assist an orthodontist, technician, or other user to adjust the rotational position of the drum relative to closure 100. Specifically, once the tip of the tool is inserted into the receiver, which may take the form of a socket or closed-ended bore, the user may exert forces to the drum to cause relative rotation of the drum relative to the closure. As discussed, this range of rotational positions may be defined by the bracket assembly's coupling mechanism 50, which is indicated somewhat schematically in FIG. 13. FIG. 12 indicates another example of surface indicia, angle indicators, or other gradations 86 that may be provided to provide a mechanism to measure and/or define the relative rotational position of the drum, and thus the prescription defined by the bracket assembly.

Bracket assembly 600 also provides another graphical illustration of a bracket assembly that includes an archwire positioning mechanism 92 that is configured to bias, or urge, the archwire within archwire slot 18. As indicated in FIGS. 12 and 13, archwire positioning mechanism 92 may take the form of a spring or resilient member that urges movement of the archwire relative to the archwire slot. However, in contrast to the archwire positioning mechanisms that were illustrated with respect to bracket assemblies 200 and 300, the archwire positioning mechanism shown in FIGS. 12 and 13 is configured to urge the archwire out of the archwire slot through the inlet 46 of the archwire slot. This force exerted upon the archwire to urge the archwire out of the archwire slot also may provide a biasing mechanism 62 (with closure member 63) that urges the drum away from the base of the bracket assembly, as indicated in FIG. 12. Since the drum is coupled to and/or received within the closure, it follows that these forces also urge the closure to an open configuration, which as discussed, may configure the drum to an adjustment position.

In the event that any patents, patent applications, or other references are incorporated by reference herein and (1) define a term in a manner that is inconsistent with and/or (2) are otherwise inconsistent with, either the non-incorporated portion of the present disclosure or any of the other incorporated references, the non-incorporated portion of the present disclosure shall control, and the term or incorporated disclosure therein shall only control with respect to the reference in which the term is defined and/or the incorporated disclosure was present originally.

As used herein, the term "and/or" placed between a first entity and a second entity means one of (1) the first entity, (2) the second entity, and (3) the first entity and the second entity. Multiple entities listed with "and/or" should be construed in the same manner, i.e., "one or more" of the entities so conjoined. Other entities may optionally be present other than the entities specifically identified by the "and/or" clause, whether related or unrelated to those entities specifically identified. Thus, as a non-limiting example, a reference to "A and/or B," when used in conjunction with open-ended language such as "comprising" may refer, in one embodiment, to A only (optionally including entities other than B); in another embodiment, to B only (optionally including entities other than A); in yet another embodiment, to both A and B (optionally including other entities). These entities may refer to elements, actions, structures, steps, operations, values, and the like.

As used herein, the phrase "at least one," in reference to a list of one or more entities should be understood to mean at least one entity selected from any one or more of the entity in the list of entities, but not necessarily including at least one of each and every entity specifically listed within the list of entities and not excluding any combinations of entities in the list of entities. This definition also allows that entities may optionally be present other than the entities specifically identified within the list of entities to which the phrase "at least one" refers, whether related or unrelated to those entities specifically identified. Thus, as a non-limiting example, "at least one of A and B" (or, equivalently, "at least one of A or B," or, equivalently "at least one of A and/or B") may refer, in one embodiment, to at least one, optionally including more than one, A, with no B present (and optionally including entities other than B); in another embodiment, to at least one, optionally including more than one, B, with no A present (and optionally including entities other than A); in yet another embodiment, to at least one, optionally including more than one, A, and at least one, optionally including more than one, B (and optionally including other entities). In other words, the phrases "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" may mean A alone, B alone, C alone, A and B together, A and C together, B and C together, A, B and C together, and optionally any of the above in combination with at least one other entity.

As used herein the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function but that the element, component, and/or other subject matter is specifically selected, created, implemented, utilized, programmed, and/or designed for the purpose of performing the function. It is also within the scope of the present disclosure that elements, components, and/or other recited subject matter that is recited as being adapted to perform a particular function may additionally or alternatively be described as being configured to perform that function, and vice versa.

As used herein, the phrase, "for example," the phrase, "as an example," and/or simply the term "example," when used with reference to one or more components, features, details, structures, embodiments, and/or methods according to the present disclosure, are intended to convey that the described component, feature, detail, structure, embodiment, and/or method is an example of components, features, details, structures, embodiments, and/or methods according to the present disclosure. Thus, the described component, feature, detail, structure, embodiment, and/or method is not intended to be limiting, required, or exclusive/exhaustive; and other components, features, details, structures, embodiments, and/or methods, including structurally and/or functionally similar and/or equivalent components, features, details, structures, embodiments, and/or methods, are also within the scope of the present disclosure.

Examples of orthodontic bracket assemblies according to the present disclosure are presented in the following enumerated paragraphs.

A1. An orthodontic bracket assembly, comprising:
a housing configured to be coupled to a patient's tooth and defining an enclosure;
a torque-adjusting drum within the enclosure and coupled for rotational movement within the housing within a range of retained positions; wherein the torque-adjusting drum defines an elongate archwire passage that is sized to receive an archwire during orthodontic use of the bracket assembly; wherein in each of the retained positions, the torque-adjusting drum defines a different prescriptive force to be applied to the patient's tooth during orthodontic use of the bracket assembly;
a positioning assembly configured to selectively retain the torque-adjusting drum within a selected retained position relative to the housing; and
a biasing mechanism configured to at least one of bias the torque-adjusting drum to a retained position and bias the torque-adjusting drum away from a retained position.

A2. The orthodontic bracket assembly of paragraph A1, wherein the bracket assembly further comprises a release mechanism configured to selectively permit adjustment of the torque-adjusting drum from the selected retained position to a different retained position of the range of retained positions; and A2.1. The orthodontic bracket assembly of paragraph A2, wherein, when actuated, the release mechanism disengages the positioning assembly to permit movement of the torque-adjusting drum away from the selected retained position and to another retained position of the range of retained positions.

A2.2. The orthodontic bracket assembly of any of paragraphs A2-A2.1, wherein the positioning assembly exerts a retaining force on the torque-adjusting drum to retain the torque-adjusting drum in a retained position, and further wherein, when actuated, the release mechanism exerts a sufficient force on the torque-adjusting drum to overcome the retaining force and to permit the torque-adjusting drum to be moved away from the selected retained position and to another retained position within the range of retained positions.

A3. The orthodontic bracket assembly of any of paragraphs A1-A2.2, wherein the torque-adjusting drum is coupled for rotational movement about an axis, and wherein rotation of the torque-adjusting drum about the axis causes relative movement of the archwire passage relative to the housing, and further wherein relative movement of the archwire passage relative to the housing changes the prescriptive force defined by the torque-adjusting drum.

A3.1. The orthodontic bracket assembly of any of paragraphs A1-A3, wherein the torque-adjusting drum includes a receiver that is sized to receive at least a tip of an adjustment tool to selectively position the torque-adjusting drum within the range of retained positions.

A3.1.1. The orthodontic bracket assembly of paragraph A3.1, wherein the receiver includes the archwire passage.

A3.1.2. The orthodontic bracket assembly of paragraph A3.1, wherein the receiver includes at least one recess that extends from the archwire passage within the torque-adjusting drum.

A3.1.3. The orthodontic bracket assembly of paragraph A3.1, wherein the receiver includes a pair of opposed recesses that extend from opposed sidewalls of the archwire passage.

A3.1.4. The orthodontic bracket assembly of paragraph A3.1, wherein the receiver includes a socket that extends within the torque-adjusting drum in a spaced-apart orientation to the archwire passage.

A3.1.5. The orthodontic bracket assembly of paragraph A3.1, wherein the receiver includes an aperture that extends through the torque-adjusting drum generally transverse to and spaced-apart from the archwire passage.

A4. The orthodontic bracket assembly of any of paragraphs A1-A3.1.5, wherein the orthodontic bracket assembly further includes a coupling mechanism that defines a path of rotational movement of the torque-adjusting drum within the enclosure.

A4.1. The orthodontic bracket assembly of paragraph A4, wherein the coupling mechanism includes at least one coupling member.

A4.2. The orthodontic bracket assembly of paragraph A4, wherein the coupling mechanism includes at least a pair of coupling members.

A4.3. The orthodontic bracket assembly of paragraph A4, wherein the coupling mechanism includes inter-engaging coupling members on the torque-adjusting drum and the housing.

A4.4. The orthodontic bracket assembly of any of paragraphs A4-A4.3, wherein the coupling mechanism further comprises at least a pair of spaced-apart stops that define the ends of the path of rotational movement of the torque-adjusting drum within the enclosure.

A5. The orthodontic bracket assembly of any of paragraphs A1-A4.4, wherein the positioning assembly is configured to interlock the torque-adjusting drum with the housing to retain the torque-adjusting drum in a selected retained position.

A5.1. The orthodontic bracket assembly of any of paragraphs A1-A5, wherein the positioning assembly includes a projecting rib on a first one of the housing and the torque-adjusting drum and a plurality of spaced-apart recesses on a second one of the housing and the torque-adjusting drum; wherein the plurality of spaced-apart recesses each are sized to receive the projecting rib, and further wherein when the projecting rib extends within a recess of the plurality of spaced-apart recesses, the torque-adjusting drum is in a restricted position and is restricted from rotating relative to the housing.

A5.1.1. The orthodontic bracket assembly of paragraph A5.1, wherein the plurality of spaced-apart recesses are spaced-apart from each other by a distance of 4-10°.

A5.1.2. The orthodontic bracket assembly of paragraph A5.1 or A5.1.1, wherein the plurality of spaced-apart recesses are spaced-apart from each other by equal increments.

A5.1.3. The orthodontic bracket assembly of paragraphs A5.1-A5.1.2, wherein the plurality of spaced-apart recesses are spaced-apart from each other by increments of 5°.

A5.1.4. The orthodontic bracket assembly of any of paragraphs A5.1-A5.1.3, wherein the positioning assembly includes a plurality of spaced-apart projecting ribs, and further wherein the plurality of spaced-apart recesses includes a greater number of recesses than the number of projecting ribs in the plurality of spaced-apart projecting ribs.

A5.1.5. The orthodontic bracket assembly of any of paragraphs A5.1-A5.1.3, wherein the projecting rib is on the housing, and the plurality of spaced-apart recesses are on the torque-adjusting drum.

A5.2. The orthodontic bracket assembly of any of paragraphs A1-A5.1.5, wherein the positioning assembly includes a pivotal latch, and the biasing mechanism biases the latch to a position for retaining the torque-adjusting drum in a selected retained position.

A5.3. The orthodontic bracket assembly of any of paragraphs A1-A5.1.5, wherein the positioning assembly includes a pivotal latch and the biasing mechanism biases the torque-adjusting drum away from the housing.

A5.3.1. The orthodontic bracket assembly of paragraph A5.3, wherein the biasing mechanism further urges an archwire out of the archwire passage.

A6. The orthodontic bracket assembly of any of paragraphs A1-A5.3.1, wherein the biasing mechanism is configured to bias the torque-adjusting drum to remain in a retained position.

A6.1. The orthodontic bracket assembly of any of paragraphs A1-A5.3.1, wherein the biasing mechanism is configured to bias the torque-adjusting drum to an adjustment position, in which the torque-adjusting drum is not within one of the retained positions and the torque-adjusting drum is rotatable to a different retained position.

A6.2. The orthodontic bracket assembly of any of paragraphs A1-A6.1, wherein the biasing mechanism includes a spring member.

A6.2.1. The orthodontic bracket assembly of paragraph A6.2, wherein the spring member extends between the torque-adjusting drum and the housing.

A6.2.1.1. The orthodontic bracket assembly of paragraph A6.2.1, wherein the spring member urges the torque-adjusting drum against the housing.

A6.2.1.2. The orthodontic bracket assembly of paragraph A6.2.1, wherein the spring member urges the torque-adjusting drum away from the housing.

A6.2.2. The orthodontic bracket assembly of any of paragraphs A6.2-A6.2.1.2, wherein the spring member couples the torque-adjusting drum to the housing to restrict removal of the torque-adjusting drum from the enclosure of the housing.

A6.2.2.1. The orthodontic bracket assembly of paragraph A6.2.2, wherein the housing includes a plurality of interconnected housing members, and further wherein the spring member extends through a passage between a pair of the housing members to restrict removal of the torque-adjusting drum from the enclosure.

A7. The orthodontic bracket assembly of any of paragraphs A1-A6.2.2.1, wherein the bracket assembly is a ligating bracket assembly.

A7.1 The orthodontic bracket assembly of any of paragraphs A1-A6.2.2.1, wherein the archwire passage includes an inlet through which an archwire is selectively inserted into the archwire passage, wherein the orthodontic bracket assembly is a ligating orthodontic bracket assembly that does not include a closure that is coupled to the housing for relative movement to selectively obstruct the inlet to prevent insertion of an archwire into the archwire passage through the inlet.

A8.1. The orthodontic bracket assembly of any of paragraphs A1-A6.2.2.1, wherein the bracket assembly is a self-ligating bracket assembly.

A8.2. The orthodontic bracket assembly of any of paragraphs A1-A6.2.2.1, wherein the archwire passage includes an inlet through which an archwire is selectively inserted into the archwire passage, wherein the orthodontic bracket assembly is a self-ligating orthodontic bracket assembly that further includes a closure that selectively obstructs the inlet to restrict removal of an archwire from the archwire passage through the inlet, and further wherein the closure is coupled to the housing for relative movement between an open configuration, in which an archwire may be inserted into the archwire passage through the inlet, and a closed configuration, in which the closure obstructs insertion of an archwire into the archwire passage through the inlet.

A8.2.1. The orthodontic bracket assembly of paragraph A8.2, wherein the closure is coupled to the housing for pivotal movement relative to the housing between the open configuration and the closed configuration.

A8.2.2. The orthodontic bracket assembly of paragraph A8.2 or A8.2.1, wherein the torque-adjusting drum is coupled to the closure for pivotal movement with the closure relative to the housing and for selective rotational movement relative to the closure.

A8.2.3. The orthodontic bracket assembly of paragraph 8.2, wherein the closure is coupled to the housing for sliding movement relative to the housing between the open configuration and the closed configuration.

A8.2.4. The orthodontic bracket assembly of any of paragraphs A8.2-A8.2.3, wherein when the closure is in an open configuration, the torque-adjusting drum is pivoted away from the housing.

A8.2.5. The orthodontic bracket assembly of any of paragraphs A8.2-A8.2.4, wherein the closure further includes an archwire positioning member that projects toward the archwire passage when the closure is in the closed configuration.

A8.2.5.1. The orthodontic bracket assembly of paragraph A8.2.5, wherein the archwire positioning member urges an archwire in the archwire passage away from the inlet of the archwire passage.

A8.2.5.2. The orthodontic bracket assembly of paragraph A8.2.5, wherein the archwire positioning member urges an archwire in the archwire passage toward the housing.

A8.2.5.3. The orthodontic bracket assembly of paragraph A8.2.5, wherein the biasing mechanism includes the archwire positioning member, and further wherein the archwire positioning member urges the torque-adjusting drum to a retained position when the closure is in the closed configuration.

A8.2.5.4. The orthodontic bracket assembly of any of paragraphs A8.2.5-A8.2.5.3, wherein the archwire positioning member includes at least one of a spring member and a resilient member.

A8.3. The orthodontic bracket assembly of any of paragraphs A8.2-A8.2.5.4, wherein the closure further includes an archwire positioning mechanism that is configured to urge the archwire within the archwire passage.

A8.3.1. The orthodontic bracket assembly of paragraph A8.3, wherein the archwire positioning mechanism forms at least a portion of the biasing mechanism.

A8.3.1.1. The orthodontic bracket assembly of any of paragraphs A8.3-A8.3.1, wherein the archwire positioning mechanism is further configured to bias the torque-adjusting drum to a retained position.

A8.3.1.2. The orthodontic bracket assembly of any of paragraphs A8.3-A8.3.1.1, wherein the archwire positioning mechanism is further configured to bias the torque-adjusting drum toward the housing.

A9. The orthodontic bracket assembly of any of paragraphs A1-A8.3.1.2, wherein at least one of the torque-adjusting drum and the housing includes indicia for indicating the rotational position of the torque-adjusting drum relative to the housing.

A9.1. The orthodontic bracket assembly of paragraph A9, wherein the indicia include gradations.

A9.2. The orthodontic bracket assembly of paragraph A9 or A9.1, wherein the indicia include a plurality of angle indicators.

A10. The orthodontic bracket assembly of any of paragraphs A1-A9, wherein the housing instead is a base of the bracket assembly.

A10.1. The orthodontic bracket assembly of any of paragraphs A1-A10, wherein the torque-adjusting drum instead is an archwire-receiving member.

A10.2. The orthodontic bracket assembly of any of paragraphs A1-A10.1, wherein the torque-adjusting drum instead is an archwire-receiving rotatable member.

A10.3. The orthodontic bracket assembly of any of paragraphs A1-A10.2, wherein the archwire passage instead is an archwire slot.

A10.4. The orthodontic bracket assembly of any of paragraphs A1-A10.3, wherein the archwire passage instead is an elongate archwire slot.

INDUSTRIAL APPLICABILITY

The orthodontic bracket assemblies and relating methods of use and orthodontic treatment that are disclosed herein are applicable to the dental and orthodontics industries.

It is believed that the disclosure set forth herein encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and subcombinations of the various elements, features, functions and/or properties disclosed herein. Similarly, when the disclosure, the preceding numbered paragraphs, or subsequently filed claims recite "a" or "a first" element or the equivalent thereof, such claims should be understood to include incorporation of one or more such elements, neither requiring nor excluding two or more such elements.

Applicant reserves the right to submit claims directed to certain combinations and subcombinations that are directed to one of the disclosed inventions and are believed to be novel and non-obvious. Inventions embodied in other combinations and subcombinations of features, functions, elements and/or properties may be claimed through amendment of those claims or presentation of new claims in that or a related application. Such amended or new claims, whether they are directed to a different invention or directed to the same invention, whether different, broader, narrower or equal in scope to the original claims, are also regarded as included within the subject matter of the inventions of the present disclosure.

The invention claimed is:

1. An orthodontic bracket assembly, comprising:
    a housing configured to be coupled to a patient's tooth and defining an enclosure;
    a torque-adjusting drum that is received within the enclosure and coupled for rotational movement with respect to the housing between a plurality of retained positions; wherein the torque-adjusting drum defines an elongate archwire passage that is sized to receive an archwire during orthodontic use of the orthodontic bracket assembly; wherein the archwire passage defines an archwire passage axis and the rotational movement is about an axis of rotation that is parallel to the archwire passage axis; wherein each respective retained position of the plurality of retained positions is pre-defined and spaced apart from each of the other respective retained positions; wherein in each retained position of the plurality of retained positions, the torque-adjusting drum defines a different prescriptive force to be applied to the patient's tooth during orthodontic use of the orthodontic bracket assembly;
    a positioning assembly configured to selectively enable translational movement of the torque-adjusting drum within the enclosure toward and away from the housing between a selected retained position of the plurality of retained positions and an adjustment position; wherein the positioning assembly includes a projecting member on a first one of the housing and the torque-adjusting drum, and a plurality of spaced-apart recesses on a second one of the housing and the torque-adjusting drum; wherein the plurality of spaced-apart recesses each are sized to receive the projecting member; wherein in each retained position of the plurality of retained positions, the projecting member extends within a corresponding recess of the plurality of spaced-apart recesses and the torque-adjusting drum is restricted from rotating relative to the housing; and further wherein in the adjustment position, the projecting member does not extend within any of the plurality of spaced-apart recesses and the torque-adjusting drum is not restricted from rotating relative to the housing; and
    a biasing mechanism configured to one of (1) bias the torque-adjusting drum toward the housing to a selected retained position of the plurality of retained positions from the adjustment position and (2) bias the torque-adjusting drum away from the housing from a retained position of the plurality of retained positions to the adjustment position.

2. The orthodontic bracket assembly of claim 1, wherein the orthodontic bracket assembly further includes a coupling mechanism that defines a path of rotational movement of the torque-adjusting drum within the enclosure, wherein the coupling mechanism includes inter-engaging coupling members on the torque-adjusting drum and the housing, wherein one of the housing and the torque-adjusting drum includes at least one first coupling member in the form of a track, guide, slide, channel, race, or gear configured to define the path of rotational movement, and the other of the housing and the torque-adjusting drum includes at least one second coupling member in the form of a gear, carriage, arm, pin, or sled configured to inter-engage with the at least one first coupling member.

3. The orthodontic bracket assembly of claim 2, wherein the coupling mechanism defines end points of the path of rotational movement of the torque-adjusting drum within the enclosure.

4. The orthodontic bracket assembly of claim 1, wherein the biasing mechanism is configured to bias the torque-adjusting drum to the selected retained position.

5. The orthodontic bracket assembly of claim 1, wherein the biasing mechanism is configured to bias the torque-adjusting drum to the adjustment position.

6. The orthodontic bracket assembly of claim 1, wherein the biasing mechanism includes a spring member, and further wherein the spring member couples the torque-adjusting drum to the housing to restrict removal of the torque-adjusting drum from the enclosure of the housing when the torque-adjusting drum is in the adjustment position and when the torque-adjusting drum is in any of the plurality of retained positions.

7. The orthodontic bracket assembly of claim 6, wherein the housing includes a plurality of interconnected housing members, and further wherein the spring member extends through a passage between a pair of the housing members to restrict removal of the torque-adjusting drum from the enclosure when the torque-adjusting drum is in the adjustment position and when the torque-adjusting drum is in any of the plurality of retained positions.

8. The orthodontic bracket assembly of claim 1, wherein the archwire passage includes an inlet through which an archwire is selectively inserted into the archwire passage, wherein the orthodontic bracket assembly is a self-ligating orthodontic bracket assembly that further includes a closure that selectively obstructs the inlet to restrict removal of the archwire from the archwire passage through the inlet, wherein the closure is configured for relative movement between an open configuration, in which the archwire may be inserted into the archwire passage through the inlet, and a closed configuration, in which the closure obstructs insertion of the archwire into the archwire passage through the inlet.

9. The orthodontic bracket assembly of claim 8, wherein the closure further includes an archwire positioning mechanism that is configured to urge the archwire within the archwire passage.

10. The orthodontic bracket assembly of claim 1, wherein the biasing mechanism couples the torque-adjusting drum to the housing to restrict removal of the torque-adjusting drum from the enclosure of the housing.

11. The orthodontic bracket assembly of claim 7, wherein the torque-adjusting drum comprises at least one drum recess formed therein, and wherein a portion of the spring member extends into the at least one drum recess.

12. The orthodontic bracket assembly of claim 8, wherein the closure is coupled to the housing.

13. The orthodontic bracket assembly of claim 8, wherein the closure is coupled to the torque-adjusting drum.

14. The orthodontic bracket assembly of claim 1, wherein the projecting member is on the torque-adjusting drum.

15. The orthodontic bracket assembly of claim 1, wherein the projecting member is an integral portion of the first one of the housing and the torque-adjusting drum.

16. The orthodontic bracket assembly of claim 1, wherein the torque-adjusting drum includes a tool receiver that is sized to receive at least a tip of an adjustment tool to adjust the position of the torque-adjusting drum relative to the housing.

17. The orthodontic bracket assembly of claim 8, wherein the biasing mechanism is configured to bias the torque-adjusting drum away from the housing to the adjustment position, and further wherein the closure includes at least one of a spring member, an elastomeric member, and a compliant member that is configured to urge an archwire, when present within the archwire passage, away from the inlet of the archwire passage and toward a wall of the archwire passage that is distal the inlet.

18. The orthodontic bracket assembly of claim 13, wherein the biasing mechanism is configured to bias the torque-adjusting drum away from the housing to the adjustment position, and further wherein the closure includes at least one of a spring member, an elastomeric member, and a compliant member that is configured to urge an archwire, when present within the archwire passage, away from the inlet of the archwire passage and toward a wall of the archwire passage that is distal the inlet.

\* \* \* \* \*